US010470944B2

(12) United States Patent
Mori et al.

(10) Patent No.: US 10,470,944 B2
(45) Date of Patent: Nov. 12, 2019

(54) UNDERPANTS-TYPE DISPOSABLE DIAPER AND PRODUCTION METHOD THEREFOR

(71) Applicant: DAIO PAPER CORPORATION, Ehime (JP)

(72) Inventors: Yosuke Mori, Ehime (JP); Sadanao Manabe, Tokyo (JP); Takashi Hagi, Ehime (JP)

(73) Assignee: DAIO PAPER CORPORATION, Shikokuchuo-Shi, Ehime (JP)

( * ) Notice: Subject to any disclaimer, the term of this patent is extended or adjusted under 35 U.S.C. 154(b) by 616 days.

(21) Appl. No.: 15/119,980

(22) PCT Filed: Feb. 26, 2015

(86) PCT No.: PCT/JP2015/055561
§ 371 (c)(1),
(2) Date: Aug. 18, 2016

(87) PCT Pub. No.: WO2015/137130
PCT Pub. Date: Sep. 17, 2015

(65) Prior Publication Data
US 2017/0049638 A1   Feb. 23, 2017

(30) Foreign Application Priority Data

Mar. 12, 2014   (JP) ................................ 2014-049108
Sep. 18, 2014   (JP) ................................ 2014-190187

(51) Int. Cl.
*A61F 13/49*   (2006.01)
*A61F 13/496*   (2006.01)
*A61F 13/15*   (2006.01)

(52) U.S. Cl.
CPC ...... *A61F 13/496* (2013.01); *A61F 13/15585* (2013.01); *A61F 13/15723* (2013.01);
(Continued)

(58) Field of Classification Search
CPC .......... A61F 13/15585; A61F 13/15747; A61F 13/49001; A61F 13/49011;
(Continued)

(56) References Cited

U.S. PATENT DOCUMENTS 6,632,211 B2 * 10/2003 Otsubo ................. A61F 13/496
                                                        604/385.22
6,991,623 B2 *  1/2006 Tanaka .............. A61F 13/49019
                                                        604/385.01
(Continued)

FOREIGN PATENT DOCUMENTS

EP          1473009 A1     11/2004
JP          11-290380 A    10/1999
(Continued)

*Primary Examiner* — Catharine L Anderson
(74) *Attorney, Agent, or Firm* — Muncy, Geissler, Olds & Lowe, P.C.

(57) ABSTRACT

A main object of the present invention is to improve the fit of edge portions of an outer body around the legs. In at least one of the ventral side outer part and the dorsal side outer part, parts at a lower edge of a side edge correspondence region corresponding to side edge portions in a front-back direction, positioned on the both width direction sides of an inner body, constitute edges of leg openings, a lower part of the side edge correspondence region is set as a folded part that is folded once or plural times in a zigzag manner in the front-back direction and fixed at the side edge portions, the folded part is gradually unfolded downward with increasing proximity to the width-direction central side, and the folded part is fixed in a halfway or completely downward unfolded state to the inner body at the width direction central portion, and elongated oblique resilient and elastic members are fixed in an extended state in a direction from the folded part to the side edges of the inner body below the folded part.

16 Claims, 28 Drawing Sheets

(52) U.S. Cl.
CPC .. *A61F 13/15747* (2013.01); *A61F 13/15764* (2013.01); *A61F 13/15804* (2013.01); *A61F 13/49001* (2013.01); *A61F 13/49011* (2013.01)

(58) Field of Classification Search
CPC ............ A61F 13/49012; A61F 13/4906; A61F 13/49061; A61F 2013/49025; A61F 2013/49026; A61F 2013/49028; A61F 2013/49063; A61F 2013/49071; A61F 2013/49073; A61F 2013/49076; A61F 2013/49082; A61F 2013/4909
See application file for complete search history.

(56) References Cited

U.S. PATENT DOCUMENTS

| | | |
|---|---|---|
| 2005/0107764 A1 | 5/2005 | Matsuda et al. |
| 2011/0288517 A1 | 11/2011 | Mori |
| 2012/0245548 A1 | 9/2012 | Matsushima et al. |
| 2017/0049637 A1* | 2/2017 | Mori ................. A61F 13/49011 |

FOREIGN PATENT DOCUMENTS

| | | |
|---|---|---|
| JP | 2005-279077 A | 10/2005 |
| JP | 2007-511326 A | 5/2007 |
| JP | 2010-162277 A | 7/2010 |
| JP | 2011-072687 A | 4/2011 |
| JP | 2011-120626 A | 6/2011 |
| JP | 2011-189068 A | 9/2011 |
| JP | 2014-004492 A | 1/2014 |
| WO | WO 2009/144875 A1 | 12/2009 |

* cited by examiner

Cross section at 6-6

Cross section at 6-6

Cross section at 7-7

Cross section at 7-7

Cross section at 6-6

Cross section at 6-6

Cross section at 7-7

Cross section at 7-7

Cross section at 6-6

Cross section at 7-7

Cross section at 6-6

Cross section at 7-7

Cross section at 6-6

Cross section at 7-7

Cross section at 6-6

Cross section at 6-6

Cross section at 7-7

Cross section at 7-7

Cross section at 6-6

Cross section at 6-6

Cross section at 7-7

Cross section at 7-7

Cross section at 6-6

Cross section at 6-6

Cross section at 7-7

Cross section at 7-7

UNDERPANTS-TYPE DISPOSABLE DIAPER AND PRODUCTION METHOD THEREFOR

TECHNICAL FIELD

The present invention relates to an underpants-type disposable diaper and a production method therefor.

As one aspect of an underpants-type disposable diaper, there has been known an underpants-type disposable diaper including an outer body formed in a cylindrical shape by joining both side portions of a ventral side outer body and both side portions of a dorsal side outer body and an inner body that is provided from a central portion of an inner surface of the ventral side outer body in a width direction to a central portion of an inner surface of the dorsal side outer body in a width direction, and absorbs excretion, wherein the ventral side outer body and the dorsal side outer body are not continuous but separated from each other on the crotch side (refer to Patent Documents 1 to 4). Such an outer halved type has the advantage that no leg openings for passage of the user's legs need to be punched or only small-area leg openings need to be punched. That is, there is the advantage that when cut pieces (hereinafter also referred to as trims) are discarded, the material loss resulting from the trims (hereinafter also referred to as trim loss) can be suppressed.

Meanwhile, there is also known an outer integral type that has an integral outer body from the ventral side to the dorsal side (for example, refer to Patent Documents 5 and 6).

However, the conventional underpants-type disposable diapers have room for improvement in fit of edge portions of the outer body around the legs. In particular, the outer halved type has the problem that the more decreased the cut areas of the leg openings to reduce trim loss, the more the fit of the edge portions around the legs is deteriorated.

CITATION LIST

Patent Document

Patent Document 1: JP-T No. 2007-511326
Patent Document 2: JP-A No. 2005-279077
Patent Document 3: JP-A No. 2010-162277
Patent Document 4: JP-A No. 2014-4492
Patent Document 5: JP-A No. 2011-189068
Patent Document 6: JP-A No. S11-290380

SUMMARY OF INVENTION

Problems to be Solved by the Invention

Accordingly, a major object of the present invention is to improve the fit of the edge portions of the outer body around the legs.

Means for Solving the Problem

The present invention to solve the foregoing problems is as follows:
<The Invention of Claim 1>
An underpants-type disposable diaper including:
an outer body that has a ventral side outer part and a dorsal side outer part and a waist opening formed by joining side edge portions of the ventral side outer part and side edge portions of the dorsal side outer part at both width direction sides; and
an inner body that has a front part joined to a width direction central area of the ventral side outer body and a back part joined to a width direction central area of the dorsal side outer body and passes through the crotch of a wearer,
edges of leg openings being at least partially formed by edges of parts of the outer body positioned on width direction both sides of the inner body, wherein,
in at least one of the ventral side outer part and the dorsal side outer part
a part at a lower edge of a side edge correspondence region corresponding to each of the side edge portions in a front-back direction, positioned on the both width direction sides of the inner body, constitutes the edge of the leg opening,
a lower part of the side edge correspondence region is set as a folded part that is folded once or plural times in a zigzag manner in the front-back direction and fixed at the side edge portions, the folded part is gradually unfolded downward with increasing proximity to the width direction central side, and the folded part is fixed in a halfway or completely downward unfolded state to the inner body at the width direction central portion, and
an elongated oblique resilient and elastic member is fixed in an extended state in a direction from the folded part to the side edge of the inner body below the folded part.
(Operation and Effect)
According to this configuration, in at least one of the ventral side outer part and the dorsal side outer part, the edges of the leg openings positioned on the lateral sides of the inner body are faced in the obliquely upward direction to the side edge portions, and the oblique resilient and elastic members are fixed in the extended state along the edges. Accordingly, the edges of the leg openings favorably fit around buttocks and groin region of the wearer.
<The Invention of Claim 2>
The underpants-type disposable diaper according to claim 1, wherein the joining between the side edge portions of the ventral side outer part and the side edge portions of the dorsal side outer part and the fixation of the folded part are integrally performed by welding process.
(Operation and Effect)
This configuration eliminates the need to fix the folded part separately.
<The Invention of Claim 3>
The underpants-type disposable diaper according to claim 1, wherein the side edge portions of the ventral side outer part and the side edge portions of the dorsal side outer part are joined by welding but are not joined by the welding at least in a region having the folded part.
(Operation and Effect)
In the present invention, the number of overlapping sheets is large in the region having the folded part out of the side edge portions. However, when the side edge portions of the ventral side outer part and the side edge portions of the dorsal side outer part are joined by welding, the joining strength varies with a locally increased number of sheets in the side edge portions, thereby resulting in reduction of productivity. Accordingly, by configuring the side edge portions so as not to be joined by welding at least in the region having the folded part as described above, the joint becomes favorably stable to prevent reduction in productivity.
<The Invention of Claim 4>
The underpants-type disposable diaper according to any one of claims 1 to 3, wherein the outer body is formed by joining the ventral side outer body constituting the ventral side outer part and the dorsal side outer body constituting the dorsal side outer part at both sides, and the ventral side outer body and the dorsal side outer body are separated from each other without being continuous at the crotch side.

(Operation and Effect)

In such an outer halved type, generally, the more decreased the cut areas of the leg openings to reduce trim loss, the more the fit of the edge portions around the legs is deteriorated. According to the present invention, however, the characteristic structure with the folded part and its unfolding allows the edges of the leg openings to fit around the buttocks and the groin region of the wearer. Accordingly, the leg openings can be formed without cutting (or with cutting) as understood from a production method described later. Therefore, the edges of the leg openings can be fitted around the groin region and the buttocks with no trim loss or less trim loss at the producing of the outer body than in the conventional diaper. In addition, conventionally, elongated resilient and elastic members are arranged obliquely or in a curved shape along the edges of the leg openings by the means of swing attachment. According to the present invention, however, the elongated resilient and elastic members can be attached obliquely without performing swing attachment as understood from the production method described later.

<The Invention of Claim 5>

The underpants-type disposable diaper according to claim 4, wherein the shape of at least one of the outer parts is rectangular with the folded part in the unfolded state.

(Operation and Effect)

By forming in this shape, the edges of the leg openings can be fitted around the groin region and the buttocks without trim loss at the producing of the outer body.

<The Invention of Claim 6>

The underpants-type disposable diaper according to claim 4 or 5, wherein the folded part is formed by being folded toward the inside of at least one of the outer parts.

(Operation and Effect)

By forming the inward folded part as described above, the unfolded portion of the folded part is unlikely to lift from the skin and is tightly fitted to the skin. In particular, when the folded part is formed in the dorsal side outer body, the unfolded portion of the folded part is shaped three-dimensionally to cover the round buttocks.

<The Invention of Claim 7>

The underpants-type disposable diaper according to claim 4 or 5, wherein the folded part is formed by folding toward the outside of at least one of the outer parts.

(Operation and Effect)

By forming the outward folded part as described above, the unfolded portion of the folded part is softly fitted to the skin by weak force.

<The Invention of Claim 8>

The underpants-type disposable diaper according to any one of claims 1 to 7, wherein the at least one of the outer parts is the dorsal side outer part.

(Operation and Effect)

In this case, the unfolded portion of the folded part covers around swelling of the buttocks. This effect is especially prominent in the invention according to claim 6.

<The Invention of Claim 9>

The underpants-type disposable diaper according to claim 8, wherein the number of folds in the folded part is an even number.

(Operation and Effect)

In this case, the unfolded portion of the folded part is wider to cover the buttocks more widely. The effect is especially prominent in the invention according to claim 6.

<The Invention of Claim 10>

The underpants-type disposable diaper according to any one of claims 1 to 8, wherein the at least one of the outer parts is the ventral side outer part, and the number of folds in the folded part is an odd number.

(Operation and Effect)

In this case, the fit to the groin region becomes favorable. The effect is especially prominent in the invention according to claim 4.

<The Invention of Claim 11>

The underpants-type disposable diaper according to any one of claims 1 to 10, wherein the folded part is formed in one of the outer parts, and the folded part is extended over the outside of the other outer part.

(Operation and Effect)

This form is suited to the case in which the angle of the edges of the leg openings is to be larger.

<The Invention of Claim 12>

A production method for an underpants-type disposable diaper, including:

an elastic belt formation step of forming a ventral side elastic belt and a dorsal side elastic belt in which elongated resilient and elastic members are fixed in an extended state to a belt-like continuous sheet material along a continuous direction thereof;

a folding step of, while conveying the ventral side elastic belt and the dorsal side elastic belt in parallel with a space therebetween in a CD direction, folding and fixing an edge side portion of at least one of the elastic belts on the side facing the other elastic belt once or plural times in a zigzag manner in the CD direction to form a folded part;

a connecting step of, after the folded part formation step, connecting a portion of the folded part closer to the forward edge than to the fold closest to the forward edge to the other elastic belt by a connecting member with a predetermined space in a MD direction;

a width increasing step of, after the connecting step, increasing a relative space between the ventral side elastic belt and the dorsal side elastic belt in the CD direction, pulling the portion of the folded part connected by the connecting member to unfold the folded part halfway or completely;

an inner body attachment step of supplying a separately produced inner body at intervals in the MD direction and joining a front part of the inner body to the ventral side elastic belt and a back part of the inner body to the dorsal side elastic belt, and fixing the unfolded portion of the folded part in the unfolded state to the inner body to form an inner assembly body;

a folding step of folding double the inner assembly body in the CD direction; and a side part joining and cutoff step of joining the ventral side elastic belt and the dorsal side elastic belt at both side parts of each individual diaper, and cutting off the ventral side elastic belt and the dorsal side elastic belt at boundaries of each individual diaper to obtain each individual diaper.

(Operation and Effect)

According to the production method, it is possible to produce the underpants-type disposable diaper described in claim 2. Accordingly, the same advantageous effects as those in the invention described in claim 2 can be provided. The term "MD direction" refers to a mechanical direction (conveyance direction), and the term "CD direction" refers to a lateral direction orthogonal to the MD direction.

<The Invention of Claim 13>

The production method for the underpants-type disposable diaper according to claim 12, wherein the number of folds is an even number at the folded part formation step.

(Operation and Effect)

In this case, the portion of the folded part closer to the forward edge than to the fold closest to the forward edge is oriented toward the opposite elastic body. Accordingly, no force acts in the detachment direction when the folded part is unfolded in the connecting member, and therefore the connecting is stable and turn-up or detachment is unlikely to occur.

<The Invention of Claim 14>

A production method for an underpants-type disposable diaper, including:

an elastic belt formation step of forming a ventral side elastic belt and a dorsal side elastic belt in which elongated resilient and elastic members are fixed in an extended state to a belt-like continuous sheet material along a continuous direction thereof;

an inner body attachment step of, while conveying the ventral side elastic belt and the dorsal side elastic belt in parallel with a space therebetween in a CD direction, supplying a separately produced inner body at intervals in a MD direction, and joining a front part of the inner body to the ventral side elastic belt and a back part of the inner body to the dorsal side elastic belt to form an inner assembly body;

a folding step of folding double the inner assembly body in the CD direction; and a side part joining and cutoff step of joining the ventral side elastic belt and the dorsal side elastic belt at both side parts of each individual diaper, and cutting off the ventral side elastic belt and the dorsal side elastic belt at boundaries of each individual diaper to obtain each individual diaper, wherein the production method further includes, after the inner body attachment step and before cutting at the boundaries of each individual diaper, a folding step of folding and fixing a portion on the leg opening side of at least one of the elastic belts once or plural times in a zigzag manner in the CD direction to form a folded part.

(Operation and Effect)

According to the production method, it is possible to an underpants-type disposable diaper providing almost the same advantageous effects as those of the underpants-type disposable diaper described in claim 1, except for the welding and fixation of the folded part. Accordingly, it is possible to provide almost the same advantageous effects as those of the invention described in claim 1. The term "MD direction" refers to a mechanical direction (conveyance direction), and the term "CD direction" refers to a lateral direction orthogonal to the MD direction.

<The Invention of Claim 15>

The production method for the underpants-type disposable diaper according to claim 14, wherein, prior to the folding step, an adhesive is applied to a site for fixing the folded part of the at least one elastic belt to fix the folded part with the adhesive at the folding step.

(Operation and Effect)

By applying the adhesive in advance to fix the folded part as described above, the folded part can be fixed directly at the time of folding. This provides the advantage that the diaper can be easily produced without having to hold the folded part in the folded state, as compared to the method by which the folded part is welded and fixed at the side part joining and cutoff step described later.

<The Invention of Claim 16>

The production method for the underpants-type disposable diaper according to claim 14, wherein, prior to the joining of the ventral side elastic belt and the dorsal side elastic belt at the side part joining and cutoff step, the folding at the folding step is performed, and while the folded state is held, the joining of the ventral side elastic belt and the dorsal side elastic belt and the fixation of the folded part are performed simultaneously by welding process.

(Operation and Effect)

According to the production method, it is possible to produce the underpants-type disposable diaper descried in claim 1. In addition, as compared to the method by which applying the adhesive in advance to fix the folded part, it is possible to eliminate the adhesion step, simplify the production process, reduce material costs by the reduction in the use of the adhesive, and suppress hardening of the outer body by the reduction in the use of the adhesive.

Advantageous Effects of Invention

As described above, according to the present invention, it is possible to provide advantages of improvement in the fit of the outer body at the edge portions around the legs.

DESCRIPTION OF EMBODIMENTS

Figure 1:
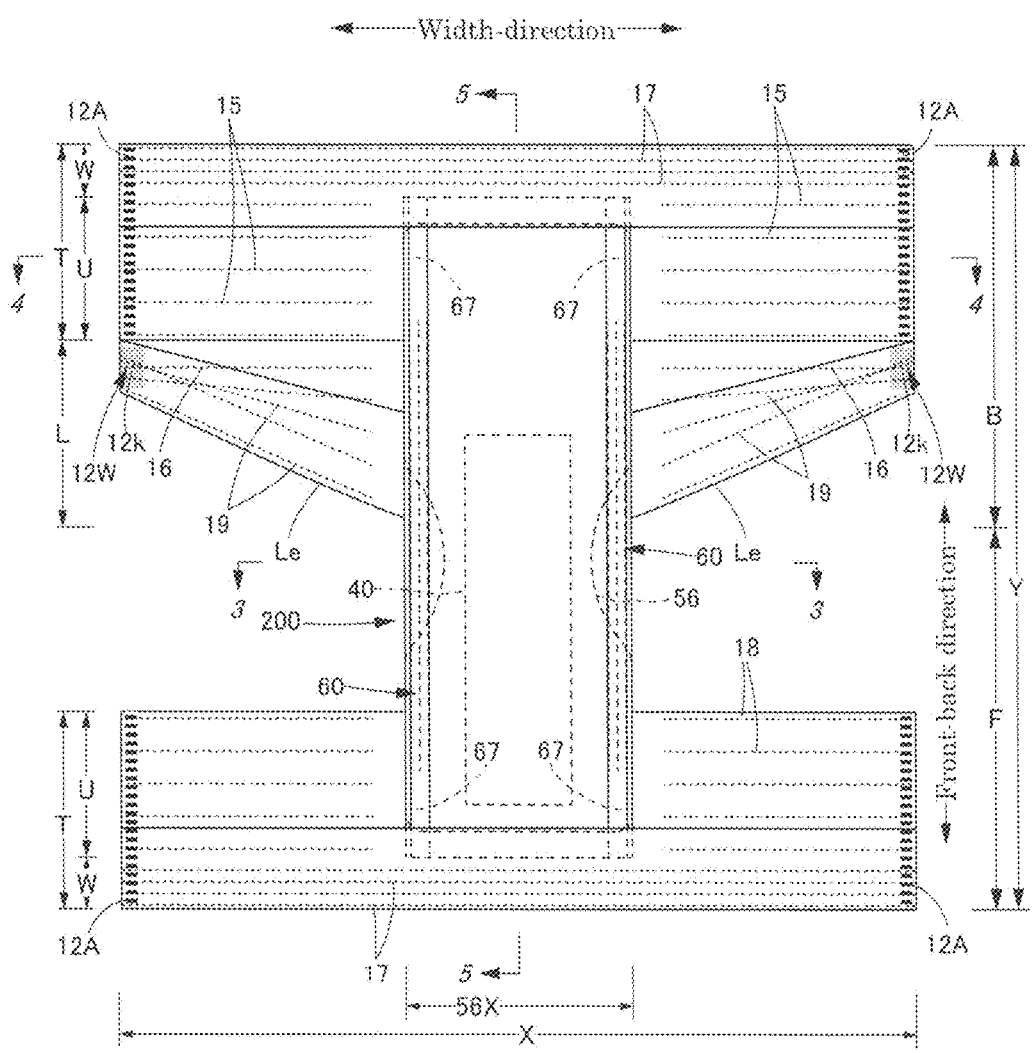
FIG. 1 is a plane view of an inner surface of an underpants-type disposable diaper in an open state.

One embodiment of the present invention will be described below with reference to the accompanying drawings.

<An Example of an Underpants-Type Disposable Diaper>

FIGS. 1 to 10(a) illustrate one example of an underpants-type disposable diaper. In this underpants-type disposable diaper, both side edges of a ventral side outer body 12F in a width direction and both side edges of a dorsal side outer body 12B in the width direction are joined along a vertical direction by heat sealing, ultrasonic welding, or the like to form cylindrical-shaped outer bodies 12F and 12B. In addition, on the outer bodies 12F and 12B, a front end portion of an inner body 200 is connected by a hot-melt adhesive or the like to an inner surface of a central portion of the ventral side outer body 12F in the width direction, and a back end portion of the inner body 200 is connected by the hot-melt adhesive or the like to the inner surface of a central portion of the dorsal side outer body 12B in the width direction. Reference sign 12A indicates a joined section (side seal portion) of the ventral side outer body 12F and the dorsal side outer body 12B. In addition, reference sign Y indicates the entire length (vertical length from an edge of a waist opening in the front panel F to an edge of the waist opening in the back panel B) of the diaper in the open state, and reference sign X indicates the entire width of the diaper in the open state.

The inner body 200 is a part absorbing and retaining excretion such as urine, and the outer bodies 12F and 12B are parts for supporting the inner body 200 for the wearer's body. The dot patterns in the drawing represent a hot-melt adhesive for joining the constituent members. Alternatively, the members may be joined by welding process (heat sealing or ultrasonic sealing). The hot-melt adhesive may be applied in a solid, bead, curtain, summit, or spiral pattern. Instead of or in addition to this, for fixation of the resilient and elastic members, the hot-melt adhesive may be applied to the outer peripheral surface of the resilient and elastic members by the means of a comb gun or a Sure-Wrap application means.

Figure 2:
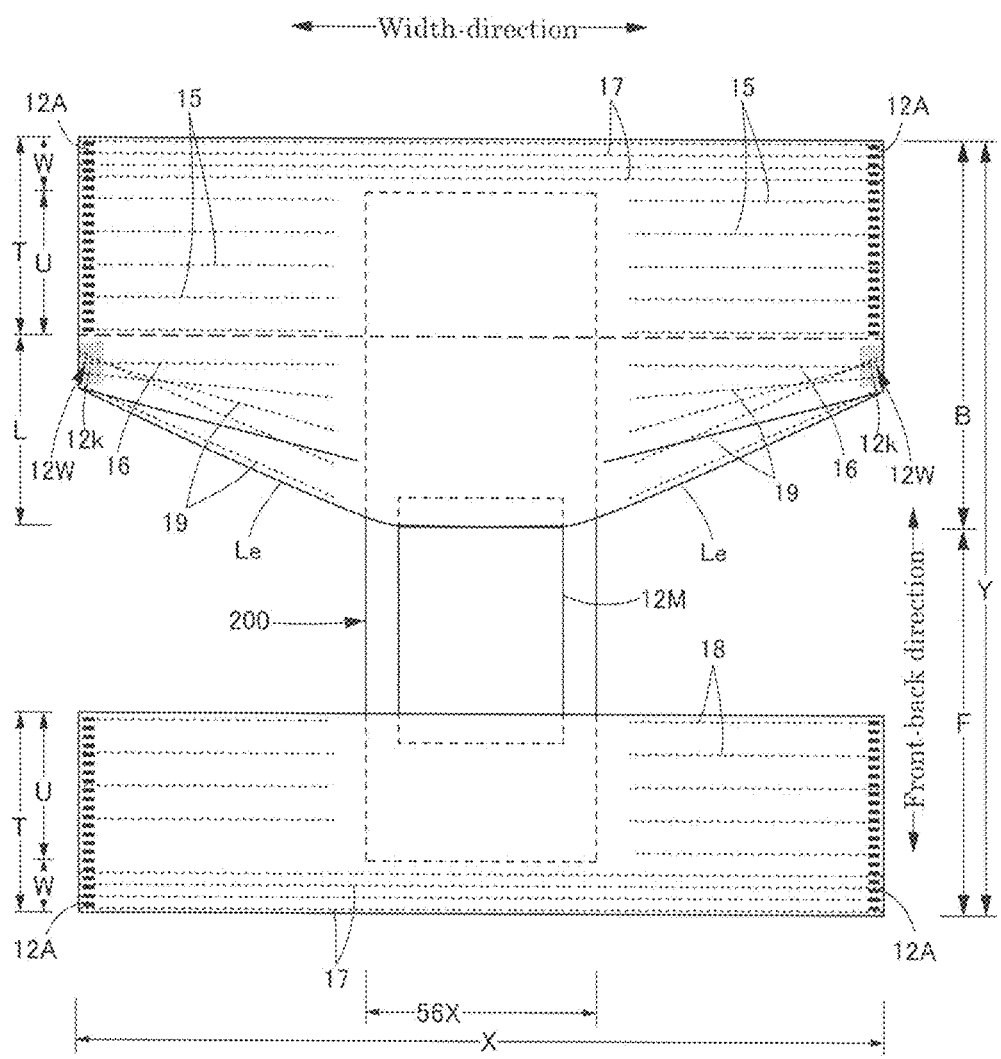
FIG. 2 is a plane view of an outer surface of the underpants-type disposable diaper in the open state.

The upper opening of the outer bodies 12F and 12B constitutes a waist opening through which the wearer's waist is passed. Parts surrounded, respectively, by lower edges of the outer bodies 12F and 12B and side edges of the inner body 200 at both sides of the inner body 200 in the width direction constitute leg openings through which the wearer's legs are passed. With respective welded portions 12A taken off and the outer bodies 12F and 12B opened, the inner body 200 has a narrower shaped intermediate portion in the front-back direction, as illustrated in FIGS. 1 and 2. The inner body 200 extends from the dorsal side to the ventral side, passing through and covering the crotch portion. The inner body 200 is a portion receiving and absorbing excretion and retaining the liquid thereof, and the outer bodies 12F and 12B are portions to support the inner body 200 to the wearer.

(Inner Body)

Figure 3:
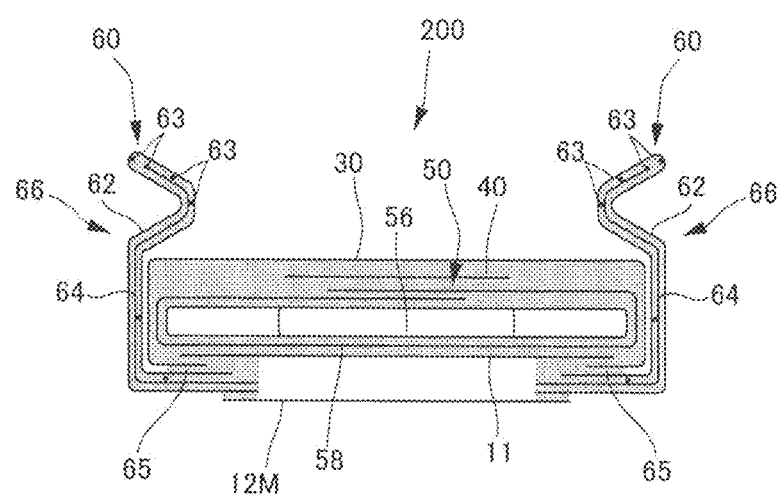
FIG. 3 is a cross-sectional view of FIG. 1 taken along line 3-3.
Figure 4:
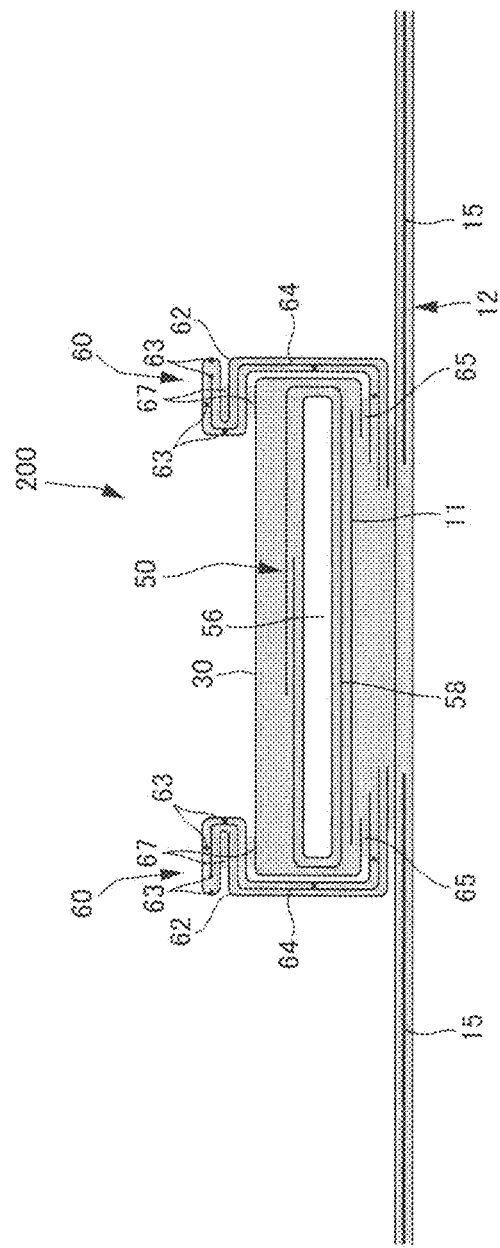
FIG. 4 is a cross-sectional view of FIG. 1 taken along line 4-4.
Figure 5:
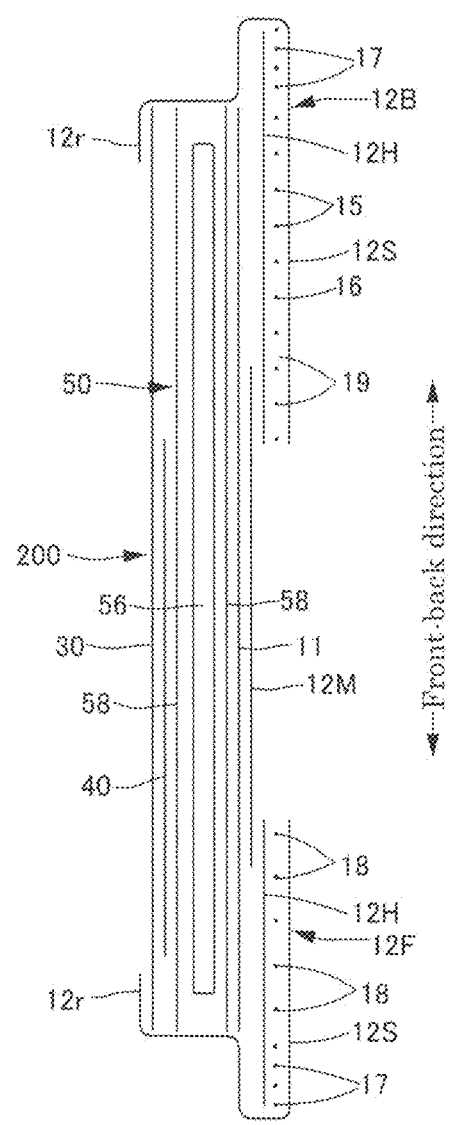
FIG. 5 is a cross-sectional view of FIG. 1 taken along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 3 to 5. Reference sign 40 indicates an interlayer sheet (second sheet) provided between the top sheet 30 and the absorbent element 50 to move quickly the liquid having passed through the top sheet 30 to the absorbent element 50 and to prevent reflowing. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.

(Interlayer Sheet)

To move the liquid having passed through the top sheet 30 quickly to the absorber, the interlayer sheet (also called as "second sheet") 40 higher in liquid permeation speed than the top sheet 30 may be provided. The interlayer sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet 40 may not be provided.

The interlayer sheet 40 may be made from the same material as that for the top sheet 30, or spun-laced, spun-bonded, SMS, or pulp non-woven fabric, or mixture sheet of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 g/m², more preferably 25 to 60 g/m². The fineness of raw fibers for the non-woven fabric is preferably 2.2 to 10 dtex. To increase the bulk of the non-woven fabric, all or some composite fibers of the raw fibers are preferably eccentric fibers with cores not centered, hollow fibers, or eccentric and hollow fibers.

The interlayer sheet 40 in the illustrated form is centered on an absorber 56 and is narrower than the absorber 56 in the width direction. Alternatively, the interlayer sheet 40 may be provided over the entire width of the absorber 56. The interlayer sheet 40 may be the same in length as the absorber 56, or may be shorter than the absorber 56, falling within the central area for receiving liquid.

(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction. Besides, the liquid impervious sheet 11 may be a non-woven fabric of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changing in color by absorption of liquid may be provided at the inside of the liquid impervious sheet 11, in particular, on the side surface of the absorber 56.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed such that a belt-like gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at a folded portion and its neighborhood. The base portions (ends opposite to the sheet folded portion in the width direction) of the three-dimensional gathers 60 positioned opposite to the forward edge portions constitute attachment portions 65 fixed to the under side surface of the inner body 200 at side edges. The portions of the three-dimensional gathers 60 other than the attachment portions 65 constitute protrusions 66 (folded portions) that protrude from the attachment portions 65. In addition, the protrusions 66 include the base portions toward the central side in the width direction and the edge portions that are folded back from the edges of the base portions toward the outside in the width direction. Although this form uses the three-dimensional gathers of surface-touching type, three-dimensional gathers (not illustrated) of a line-touching type that are not folded back toward the outside in the width direction may also be used. Then, while the both ends of the protrusions 66 in the front-back direction are front-back fixed portions 67 which are fixed to the side surfaces of the top sheet 30 in a lying down state with a hot-melt adhesive or a heat seal, the intermediate portions positioned therebetween are unfixed free portions to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m². The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60$d$ is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 6:
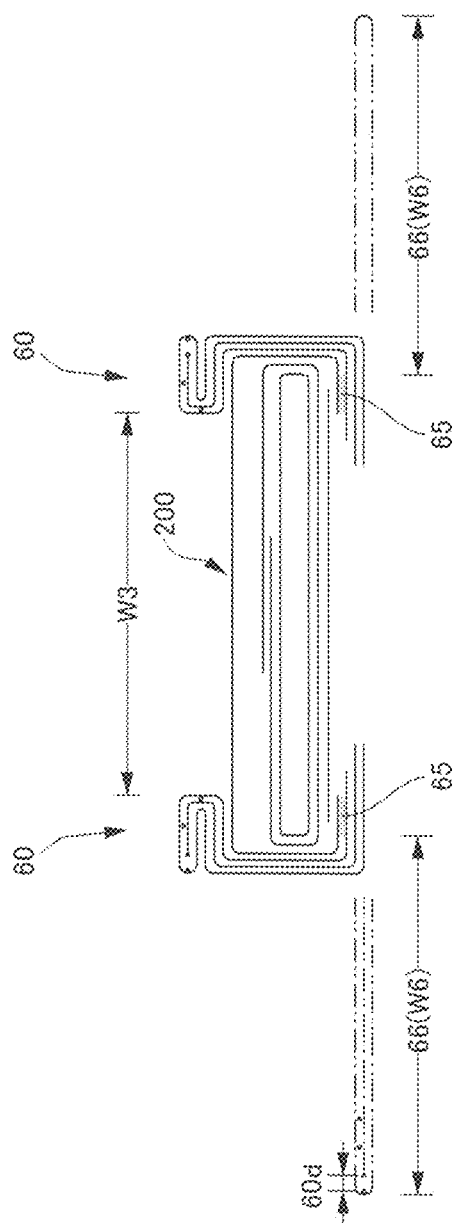
FIG. 6 is a cross-sectional view of major parts of the underpants-type disposable diaper together with dimensions.
Figure 7:
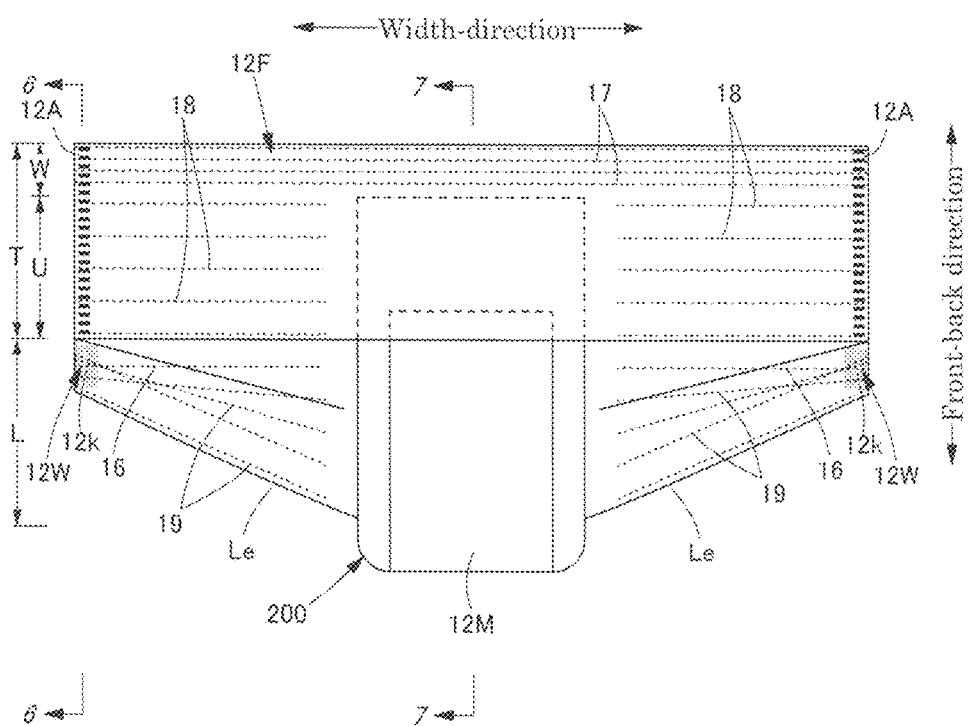
FIG. 7 is a front view of the underpants-type disposable diaper in the open state.
Figure 8:
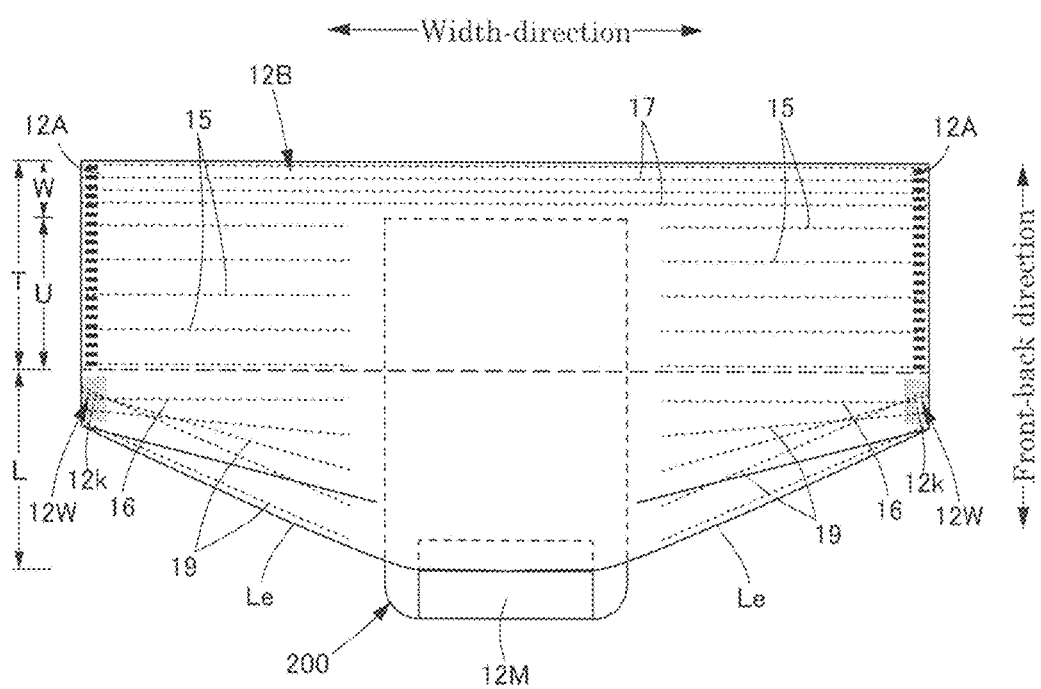
FIG. 8 is a back view of the underpants-type disposable diaper in the open state.
Figure 9:
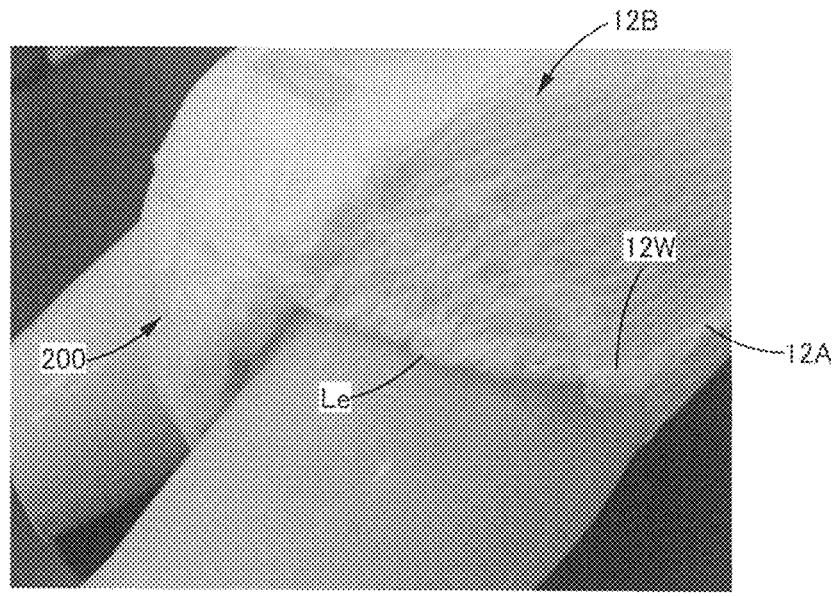
FIGS. 9(*a*) and 9(*b*) are photographs of samples of underpants-type disposable diapers.
Figure 9:
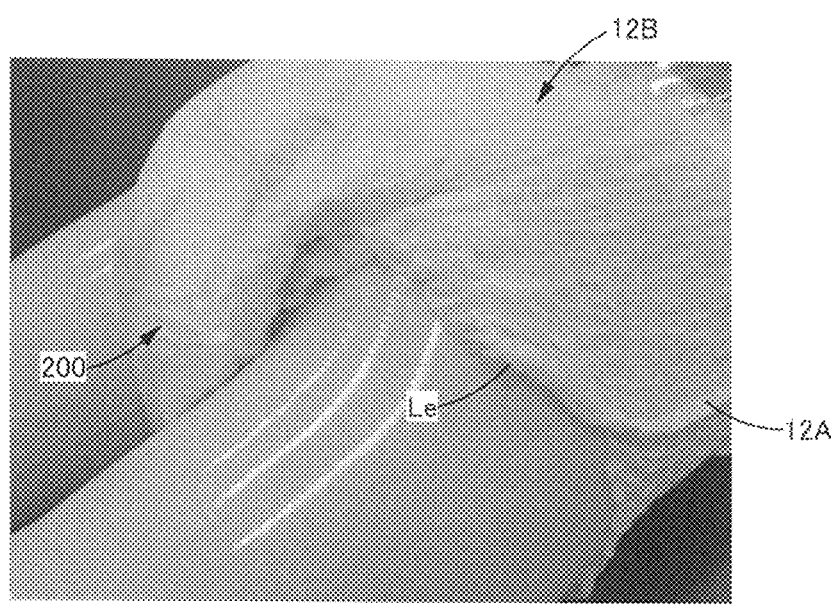
Figure 10:
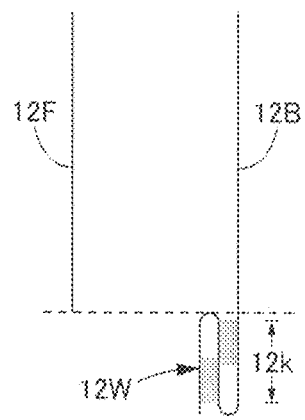
FIGS. 10(*a*) and (*b*) are schematic cross-sectional views of various forms at a position taken along line 6-6 and a position taken along line 7-7 of FIG. 7.
Figure 10:
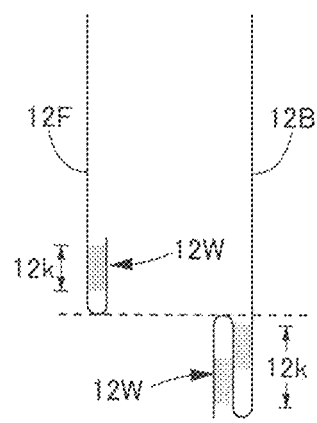
Figure 10:
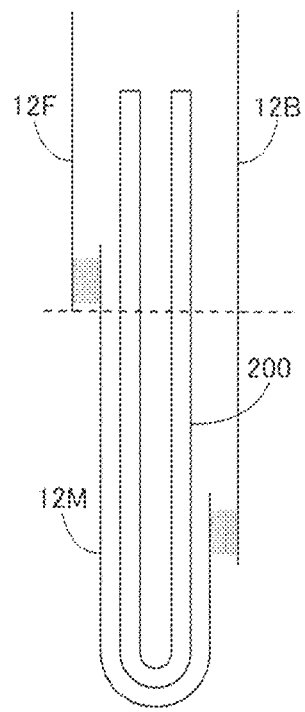
Figure 10:
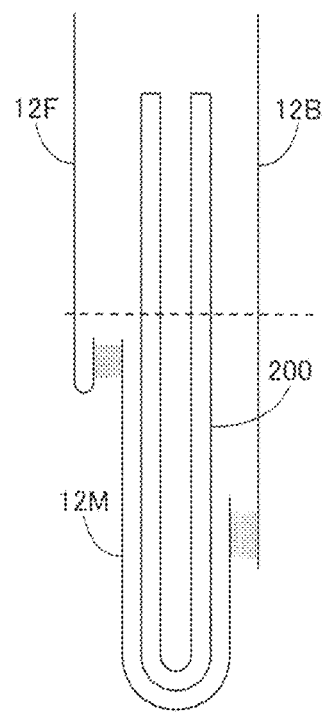
Figure 11:
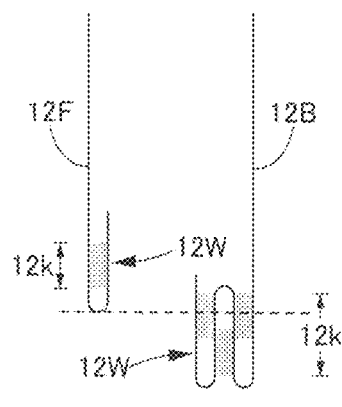
FIGS. 11(*a*) and (*b*) are schematic cross-sectional views of various forms at the position taken along line 6-6 and the position taken along line 7-7 of FIG. 7.
Figure 11:
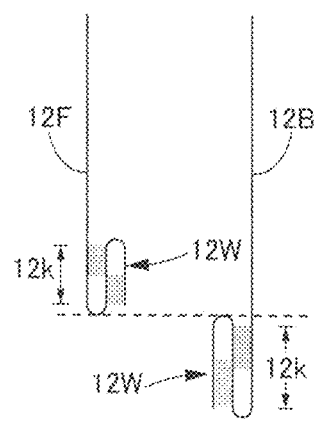
Figure 11:
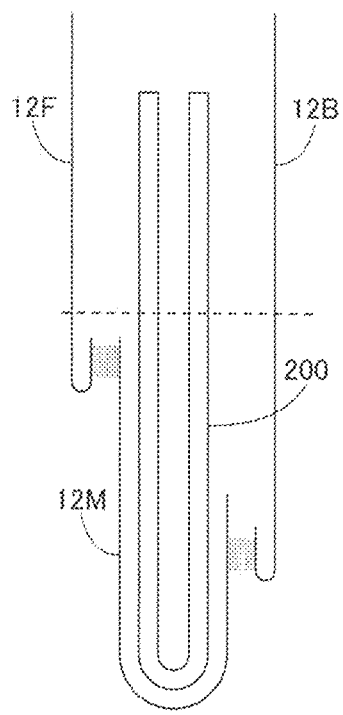
Figure 11:
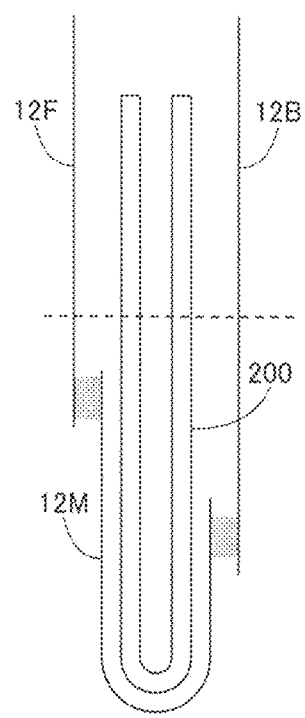
Figure 12:
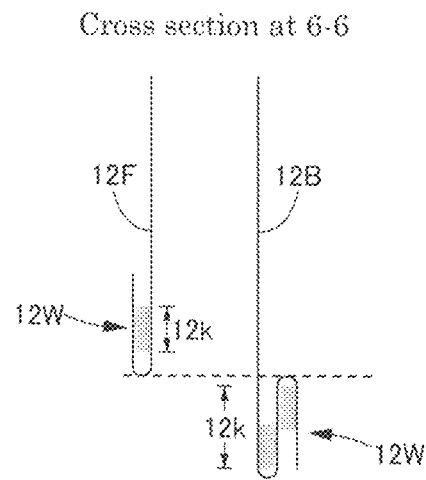
FIGS. 12(*a*) and (*b*) are schematic cross-sectional views of various forms at the position taken along line 6-6 and the position taken along line 7-7 of FIG. 7.
Figure 12:
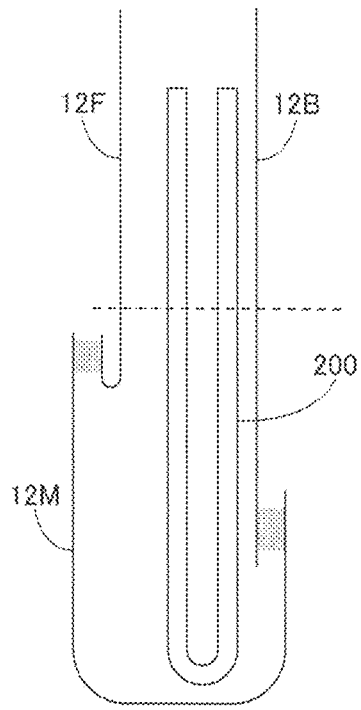
Figure 12:
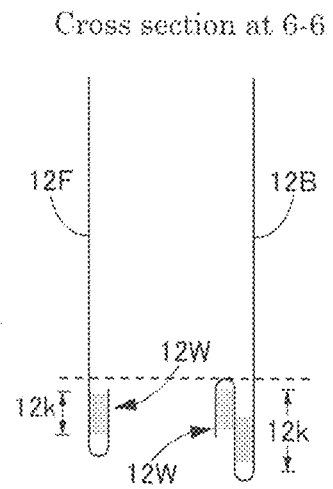
Figure 12:
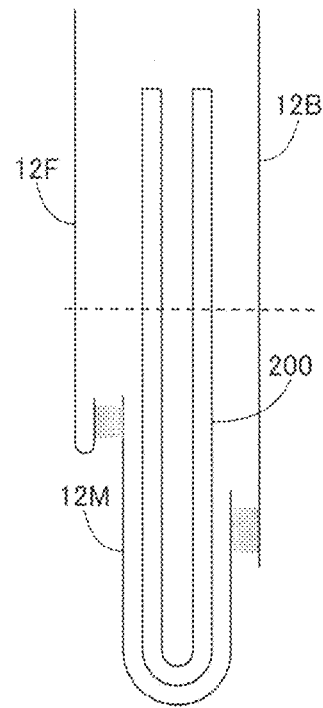

The dimensions of the three-dimensional gathers 60 can be decided as appropriate. In the case of a disposable diaper for infants, however, the standing height W6 (width of the protrusions 66 in an open state) is preferably 15 to 60 mm, more specifically 20 to 40 mm as illustrated in FIG. 6, for example. In addition, the separation distance W3 between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

The absorber 56 may be rectangular in shape but preferably has an hourglass shape having a front end portion, a back end portion, and a narrower portion that is positioned between the front and back end portions and is narrower than the two end portions as illustrated in FIG. 1 to improve the absorber 56 and the three-dimensional gathers 60 in a fit of the edges around the legs.

The dimensions of the absorber 56 can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "powders" as well as "particles". The diameter of the high-absorbent polymer particles 54 may be the same as that of particles for general use in this type of absorbent article. For example, the ratio of particles that remain on a sieve after sieving (shaking for five minutes) with a standard sieve (JIS Z8801-1:2006) of 500 μm is preferably 30 weight % or less. Alternatively, the ratio of particles that remain on the sieve after sieving (shaking for five minutes) with the standard sieve (JIS Z8801-1:2006) of 180 μm is preferably 60 weight % or more.

There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylic acid (salt) graft copolymer, a saponified material of starch-acrylonitrile copolymer, a crosslinking substance of carboxymethyl-cellulose sodium, an acrylic acid (salt) polymer, or the like. The high-absorbent polymer particles are preferably used in a general particulate form but may be used in another form.

The water absorption rate of the high-absorbent polymer particles is preferably 70 seconds or less, more preferably 40 seconds or less. When the water absorption is too late, the liquid, which has supplied to the absorber 56, is more likely to flow back to the outside of the absorber 56 (so called "reflowing").

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Crotch Portion Cover Sheet)

To the back surface of the liquid impervious sheet in the inner body 200 can be attached a crotch portion cover sheet 12M so as to cover a part of exposed portion of the inner body 200 (for example, along the entire front-back direction of the exposed portion between the ventral side outer body 12F and the dorsal side outer body 12B but not extending to the front and back ends of the inner body 200, or both side edges in the width direction not reaching the both side edges of the inner body 200) or the entire inner body 200. A material for the crotch portion cover sheet 12M similar to that of the outer bodies 12F and 12B may be used as explained below.

(Outer Body)

The outer bodies 12F and 12B have waist portions T having the side seal portions 12A and determined as vertical areas (vertical areas from the waist opening to the upper ends of the leg openings) and an intermediate portion L determined as a front-back area of a portion forming the leg openings (between a vertical region of the ventral-side outer body 12F having the side seal portions 12A and a vertical region of the back-side outer body 12B having the side seal portions 12A). The waist portions T are conceptually divided into "waist edge portions" W forming the edge of the waist opening and "lower waist portions" U as the portions under the waist edge portions W. Normally, when there are boundaries at which stretching stress in the width direction changes (for example, the thickness or the extension ratio of resilient and elastic members changes) in the waist portions T, portions closer to the waist opening WO than to boundaries closest to the waist opening WO correspond to the waist edge portions W. When there are no boundaries like this, portions closer to the waist opening WO than to the absorber 56 or to the inner body 200 correspond to the waist edge portions W. The lengths of these portions in the vertical direction vary depending on the size of the product and can be decided as appropriate. As an example, the length of the waist edge portion W may be 15 to 40 mm, and the length of the lower waist portion U may be 65 to 120 mm. On the other hand, the intermediate portion L can be also omitted or the intermediate portions L can be provided on both of the ventral-side outer body and the back-side outer body. In the form illustrated in the drawings, the intermediate portion L is provided on only the back-side outer body 12B and covers buttocks. When the edges of the intermediate portion L at the leg sides are formed into curved shapes so as to be along the circumferences of the legs, the fit to the circumferences of the legs are excellent and it is therefore preferable.

The outer bodies 12F and 12B are constituted by the ventral-side outer body 12F and the back-side outer body 12B, and the ventral-side outer body 12F and the back-side outer body 12B are not continuous at the leg sides and are separated from each other. A separation distance L8 therebetween may be set to approximately 150 to 250 mm.

The outer body 12 is formed by joining the two sheet materials 12S and 12H with an adhesive such as a hot-melt adhesive as illustrated in FIGS. 3 to 5. The inner sheet material 12H positioned inside extends up to the edge of the waist opening, whereas the outer sheet material 12S wraps around the edge of the inner sheet material 12H on the waist side and folds back toward the inside. Folded part 12w is extended to cover the upper end portion of the inner body 200 on the waist side.

There is no specific limitation on the sheet materials 12S and 12H as far as they are sheet-like, but they are preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. When the non-woven fabric is used, it is preferable that the basis weight thereof is approximately 10 to 30 g/m$^2$.

Also as illustrated in FIGS. 2 and 5, in the ventral side outer body 12F and the dorsal side outer body 12B, elongated resilient and elastic members 15 to 19 are provided at a predetermined extension ratio between both the sheet materials 12S and 12H, in order to enhance the fit around the wearer's waist.

The elongated resilient and elastic members 15 to 19 may be made from a synthetic rubber or a natural rubber. In addition, the resilient and elastic members 15 to 19 may be elongated like threads, strings, or belts, or may be net-like or sheet-like. To stick the two sheet materials 12S and 12H of the outer bodies 12F and 12B and fix the elongated resilient and elastic members 15 to 19 sandwiched between the sheet materials 12S and 12H, a hot-melt adhesive can be used by various application methods, or heat sealing or ultrasonic adhesion can be used.

When the elongated resilient and elastic members 15 to 19 are used, same resilient and elastic members can be uniformly provided. It is preferable, however, to make fineness, spacing, or the like different depending on a position of the outer bodies 12F and 12B. Thus, in the illustrated form, a plurality of waist edge resilient and elastic members 17 is fixed at the waist edge portion W in the extended state along the width direction at a predetermined extension ratio with spacing therebetween in the up-down direction in such a manner as to be entirely continuous in the width direction. One or more of the waist edge resilient and elastic members 17 in a region adjacent to the lower waist portion U may overlap the inner body 200 or may be provided on a lateral side of a center portion in the width direction overlapping with the inner body 200 so as to be continuous in the width direction. As the waist edge resilient and elastic members 17, about 3 to 22 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 150 to 400%, in particular about 220 to 320%, with spacing of 4 to 12 mm. All of the waist edge resilient and elastic members 17 may not be equal in thickness and extension ratio. For example, the resilient and elastic members may be different in fineness and extension ratio between the upper and lower sides of the waist edge portions W.

In the lower waist portions U, a plurality of lower waist portion resilient and elastic members 15 and 18 composed of elongated resilient and elastic members is fixed in the extended state along the width direction at a predetermined extension ratio with up-down direction space therebetween in such a manner as to be entirely continuous in the width direction, at upper sides and at the lateral sides of central portions of the lower waist portions U in the width direction overlapping the inner body 200.

As the lower waist portion resilient and elastic members 15 and 18, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, with spacing of 1 to 15 mm, in particular 3 to 8 mm.

Characteristically, as illustrated in FIG. 10(a), the intermediate portion L in the dorsal side outer body 12B is folded once or plural times in a zigzag manner in the front-back direction at the side edge and fixed by a hot-melt adhesive or the like to form a folded part 12W. The folded part 12W is gradually unfolded downward with increasing proximity to the width-direction central portion, and the folded part 12W is fixed by a hot-melt adhesive or the like to the inner body 200 in a halfway or completely downward unfolded state at the width-direction central portion. The fixed portion of the folded part 12W is shown with reference sign 12k. In addition, oblique resilient and elastic members 19 composed of elongated resilient and elastic members fixed in the extended state are provided in the direction from the folded part 12W to the side edge under the folded part 12W in the inner body 200. The oblique resilient and elastic members 19 are provided on the lateral sides of the the width direction overlapping the inner body 200, and are set along the width direction when the folded part 12W is unfolded. In the illustrated form, on the upper portion of the intermediate portion L, a plurality of intermediate portion resilient and elastic members 16 constituted of elongated resilient and elastic members continuous in the width direction is fixed at up-down direction intervals and in the state extended along the width direction at a predetermined extension ratio on the lateral sides of the width direction central portion overlapping the inner body 200.

By including the oblique resilient and elastic members 19 in addition to the folded and unfolded structure, edges Le of the leg openings disposed on the lateral sides of the inner body 200 are faced in an obliquely upward direction toward the side edge portions in the dorsal side outer body 12B, and the oblique resilient and elastic members 19 are fixed in the extended state along the edges. Accordingly, the edges Le of the leg openings fit closely and favorably around the round buttocks of the wearer. FIG. 9(a) is a photograph of a dummy doll wearing a sample in the form illustrated in FIGS. 1 to 8 and 10(a). FIG. 9(b) is a photograph of a dummy doll wearing an outer halved-structure commercial product not having the folded and unfolded structure or the oblique resilient and elastic members 19. As seen from the comparison between these examples, the sample according to the present invention has the edges Le of the leg openings in the dorsal side outer body 12B fitting favorably to the round buttocks and covering favorably the buttocks, as compared to the commercial products.

The folded part 12W and the oblique resilient and elastic members 19 may be provided only on the dorsal side outer body 12B as illustrated in FIGS. 10(a), 13, 20, and 21(a), as well as on both the ventral side outer body 12F and the dorsal side outer body 12B as illustrated in FIGS. 10(b), 11, 12, and 22. In addition, the folded part 12W and the oblique resilient and elastic members 19 may be provided only on the ventral side outer body 12F as illustrated in FIG. 21(b).

The folded part 12W may be folded in a direction toward the inside of the diaper as illustrated in FIGS. 10, 11, 12(b), 13, 20, and 21(b), as well as in a direction toward the outside of the diaper as illustrated in FIGS. 12(a) and 21(a). When the folded part 12W is formed by folding inward as in the former case, the unfolded portion of the folded part 12W is unlikely to lift from the skin and fits tightly to the skin. In particular, when the folded part 12W is provided in the dorsal side outer body 12B, the unfolded portion of the folded part 12W is formed in a three-dimensional shape to cover the round buttocks. Meanwhile, when the folded part 12W is formed by folding outward as in the latter case, the unfolded portion of the folded part 12W fits softly to the skin by weak force.

Figure 20:
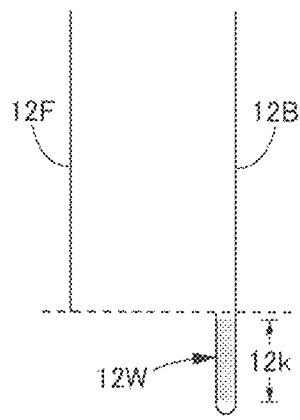
FIGS. 20(*a*) and (*b*) are schematic cross-sectional views of various forms at the position taken along line 6-6 and the position taken along line 7-7 of FIG. 18.
Figure 20:
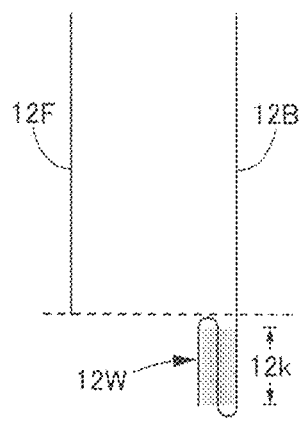
Figure 20:
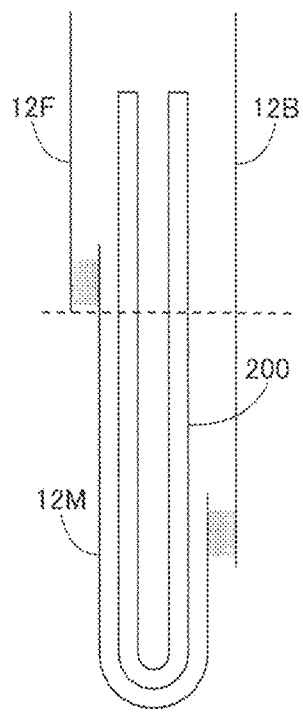
Figure 20:
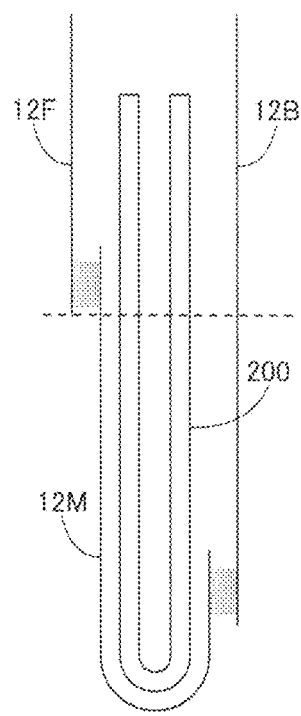
Figure 21:
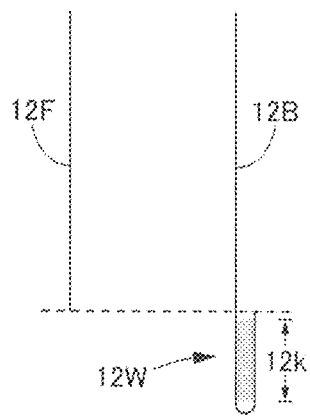
FIGS. 21(a) and (b) are schematic cross-sectional views of various forms at the position taken along line 6-6 and the position taken along line 7-7 of FIG. 18.
Figure 21:
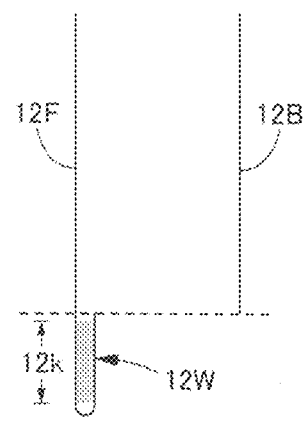
Figure 21:
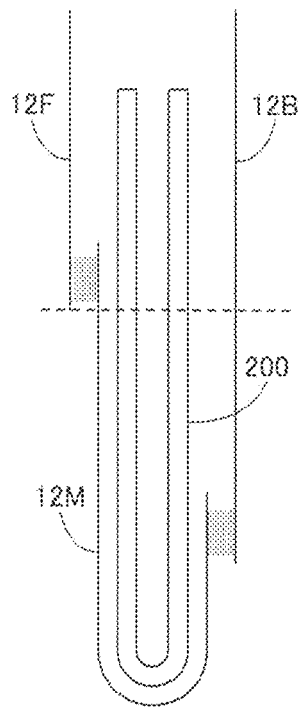
Figure 21:
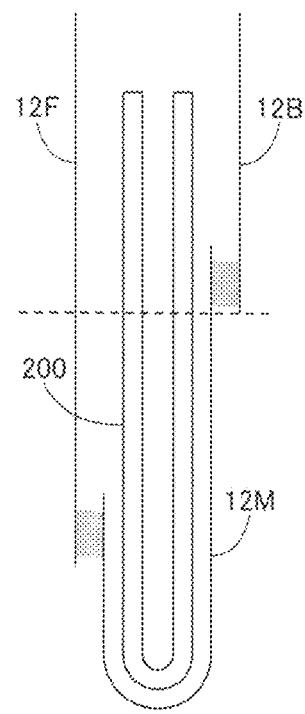
Figure 22:
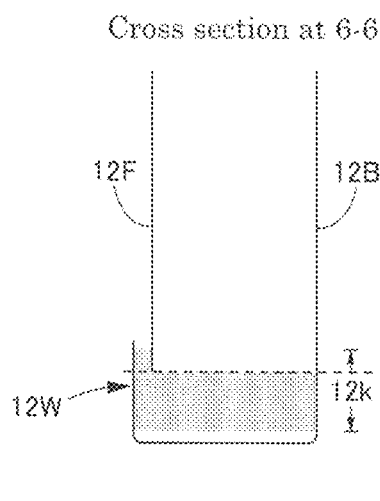
FIGS. 22(a) and (b) are schematic cross-sectional views of various forms at the position taken along line 6-6 and the position taken along line 7-7 of FIG. 18.
Figure 22:
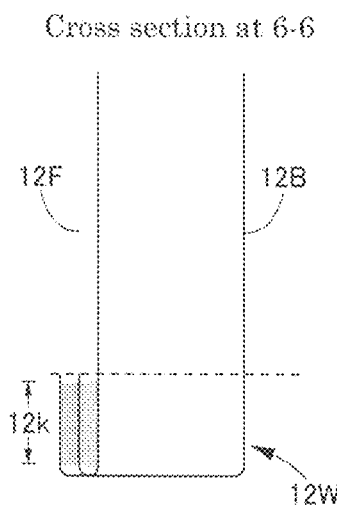
Figure 22:
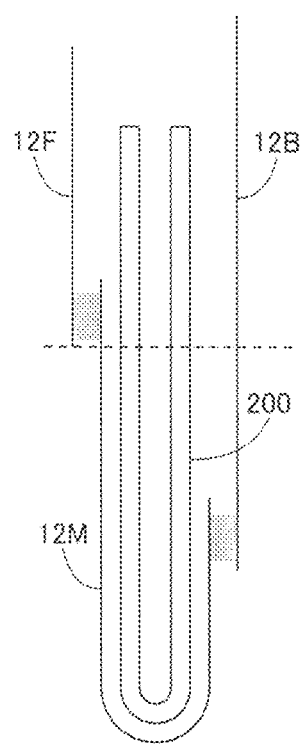
Figure 22:
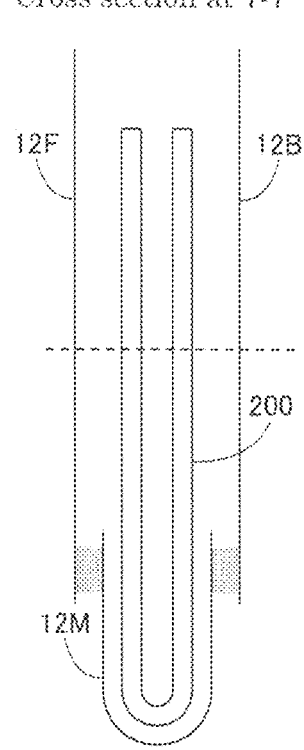

The number of folds in the folded part 12W can be decided as appropriate, and is preferably one as illustrated in FIGS. 20(a), 21, and 22 when the diaper is produced by a production method shown in FIGS. 25 to 28 described later. Meanwhile, when the folded part 12W is provided in the dorsal side outer body 12B as illustrated in FIGS. 10, 11(b) to 13, 20, and 21(a), forming an even number of folds widens the unfolded portion of the folded part 12W to cover the buttocks more widely. This effect is more significant in particular when the folded part 12W is folded in the direction toward the inside of the diaper.

In addition, as illustrated in FIGS. 10(b), 11(a), 12, 21(b), and 22, when the folded part 12W is provided in the ventral side outer body 12F, forming an odd number of folds allows the edges Le of the leg openings to enter into the valley of the human body while wrapping the round body part, thereby providing a favorable fit to the groin region. This effect is more significant in particular when the folded part 12W is folded in the direction toward the inside of the diaper.

The folded part 12W may be positioned under the side seal portions 12A as illustrated in FIGS. 10(a), 12(b), 13, 20, 21, and 22(b). Specifically, the folded part 12W may be configured such that the outer body forming the folded part 12W is extended toward the leg opening side beyond the other outer body and the extended portion is folded as illustrated. In addition, the folded part 12W may overlap partially or entirely the side seal portions 12A as illustrated in FIGS. 10(b), 11, 12(a), 22(a), and 24. As a form similar to the latter one, both the ventral side outer body 12F and the dorsal side outer body 12B may be integrally folded to the ventral side (or the dorsal side) as illustrated in FIG. 12(b).

Figure 13:
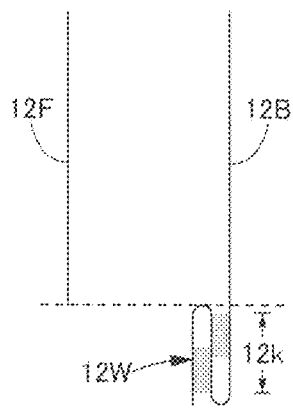
FIG. 13 are schematic cross-sectional views of various forms at the position taken along line 6-6 and the position taken along line 7-7 of FIG. 7.
Figure 13:
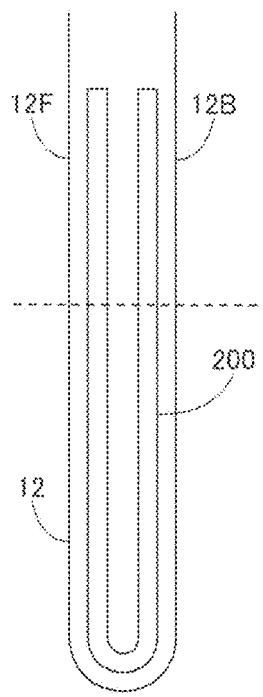

The side seal portions 12A may be formed including the folded part 12W as illustrated in FIGS. 10(b) to 12(a). However, in the case of forming the side seal portions 12A by welding, when the number of overlaps in the sheet at the side seal portions 12A is locally large, the joining strength may vary resulting in risk of reducing productivity. Accordingly, the side seal portions 12A are preferably not formed in the leg opening side region having the folded part 12W as illustrated in FIGS. 10(a), 12(b), and 13. Accordingly, the side seal portions 12A can be stably joined to prevent reduction in productivity.

Figure 23:
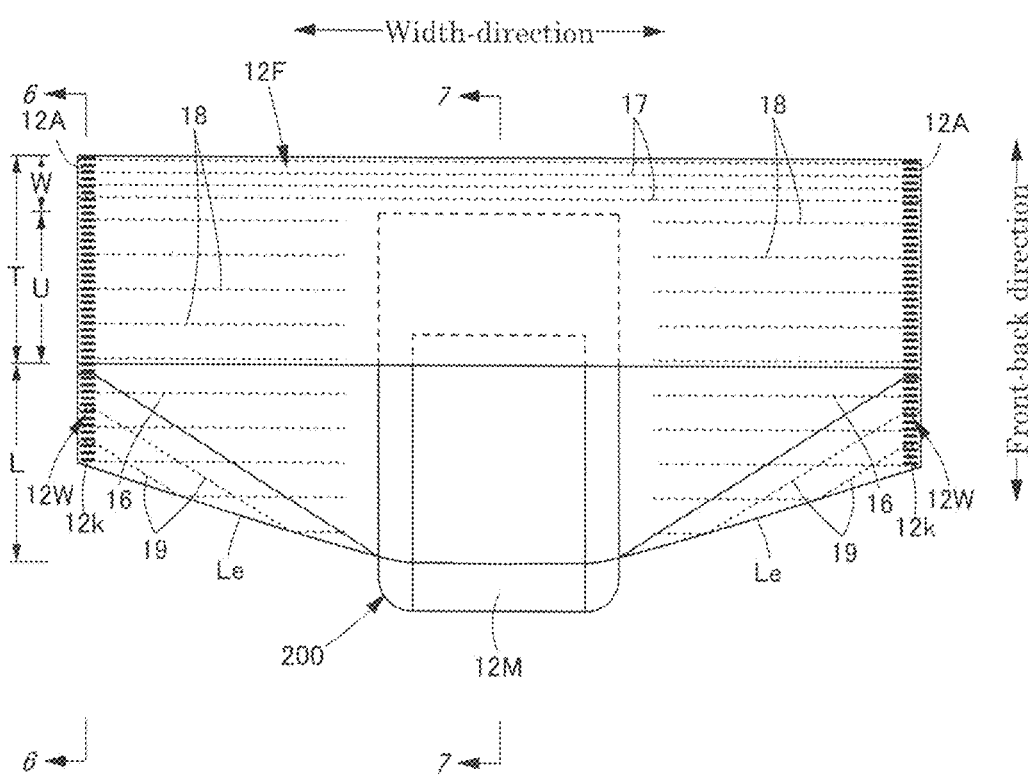
FIG. 23 is a front view of an underpants-type disposable diaper in the open state.

The folded part 12W may be fixed with an adhesive 12p and by welding process such that the folded part 12W is first fixed with the adhesive 12p and then the side seal portions 12A and the folded part 12W are integrally welded as illustrated in FIGS. 18 to 20(a). Otherwise, the folded part 12W may be fixed by welding integrally with the side seal portions 12A without the use of the adhesive as illustrated in FIG. 23. When the folded part 12W is positioned under the side seal portions 12A as illustrated in FIGS. 18 to 20(a), only the side seal portions 12A may be welded and the folded part 12W may be fixed only with the adhesive, although not illustrated.

The dotted lines in FIGS. 10 to 13 and 20 to 22 represent the lower end of the side seal portions 12A. For example, in the dorsal side outer body 12B illustrated in FIG. 10(a), the waist portion T and the intermediate portion L are corresponding to the side edge correspondence region in the present invention, and the intermediate portion L is corresponding to the lower side portion (leg side portion) of the side edge correspondence region in the present invention, respectively. In the ventral side outer body 12F illustrated in FIG. 10(b), the waist portion T is corresponding to the side edge correspondence region in the present invention, and the lower side portion (leg side portion) of the waist portion T is corresponding to the lower side portion of the side edge correspondence region in the present invention, respectively. In the dorsal side outer body 12B illustrated in FIG. 11(a), the waist portion T and the intermediate portion L are corresponding to the side edge correspondence region, and the lower end portion of the waist portion T and the intermediate portion L are corresponding to the lower side portion of the side edge correspondence region, respectively.

In addition, the dot patterns in FIGS. 10 to 13 and 20 to 22 represent the hot-melt adhesive for fixing the ventral side outer body 12F and the dorsal side outer body 12B to the inner body, and the hot-melt adhesive for fixing the folded part.

On the other hand, according to the folded and unfolded structure of the present invention, as described above, the edges Le of the leg openings obliquely face up to the edge portions. Thus, the edges Le of the leg openings are not cut to fit around the wearer's legs, instead the edges can be formed around the wearer's legs even by configuring the ventral side outer body 12F and the dorsal side outer body 12B to be rectangular in shape in a state where the folded part 12W is unfolded. Yet in this case, as can be seen from a producing method described later, trim loss in the producing of the outer bodies 12F and 12B can be completely eliminated.

As the intermediate resilient ad elastic members 16 and the oblique resilient and elastic members 19, about 2 to 10 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 150 to 300%, in particular about 180 to 260%, with spacing of 5 to 40 mm, in particular 5 to 20 mm.

When the lower waist portion resilient and elastic members 15, 18 and the intermediate portion resilient and elastic members 16 and the oblique resilient and elastic members 19 are provided at the both sides of the central portions overlapping the inner body 200 in the width direction except for the central portions as illustrated in the drawings, the inner body 200 does not contract more than necessary in the width direction, thus the diaper does not become rough with deterioration in appearance and does not decrease in absorbing performance. The foregoing form includes the form in which the resilient and elastic members reside only at the both sides in the width direction, and the form in which the resilient and elastic members reside crossing over the inner body 200 from one side to the other side in the width direction, but the resilient and elastic members are finely cut and exert no contraction force at the central portion overlapping the inner body 200 in the width direction (this substantially means that no resilient and elastic members are provided), and thus the contraction force of the resilient and elastic members acts only at the both sides in the width direction. As a matter of course, the arrangement forms of the lower waist portion resilient and elastic members 15, 18 and the intermediate portion resilient and elastic members 16 and the oblique resilient and elastic members 19 are not limited to the foregoing examples. Alternatively, some or all of the lower waist portion resilient and elastic members 15, 18 and the intermediate portion resilient and elastic members 16 and the oblique resilient and elastic members 19 may be provided crossing over the inner body 200 from the one side to the other side in the width direction so that the stretching force acts on the entire lower waist portions U in the width direction.

(Others)

The foregoing example is based on an outer halved structure in which the ventral side outer body 12F and the dorsal side outer body 12B are separated from each other. However, as illustrated in FIG. 13, the foregoing example is also applicable to an outer body 12 that is continuous from the ventral side to the dorsal side via the crotch. The ventral side region and dorsal side region in the continuous outer body 12 are corresponding to the ventral side outer body 12F and the dorsal side outer body 12B. Accordingly, in the present invention, they are connectively called ventral side outer part and dorsal side outer part.

<Example of a Method of Producing the First Form>

Figure 14:
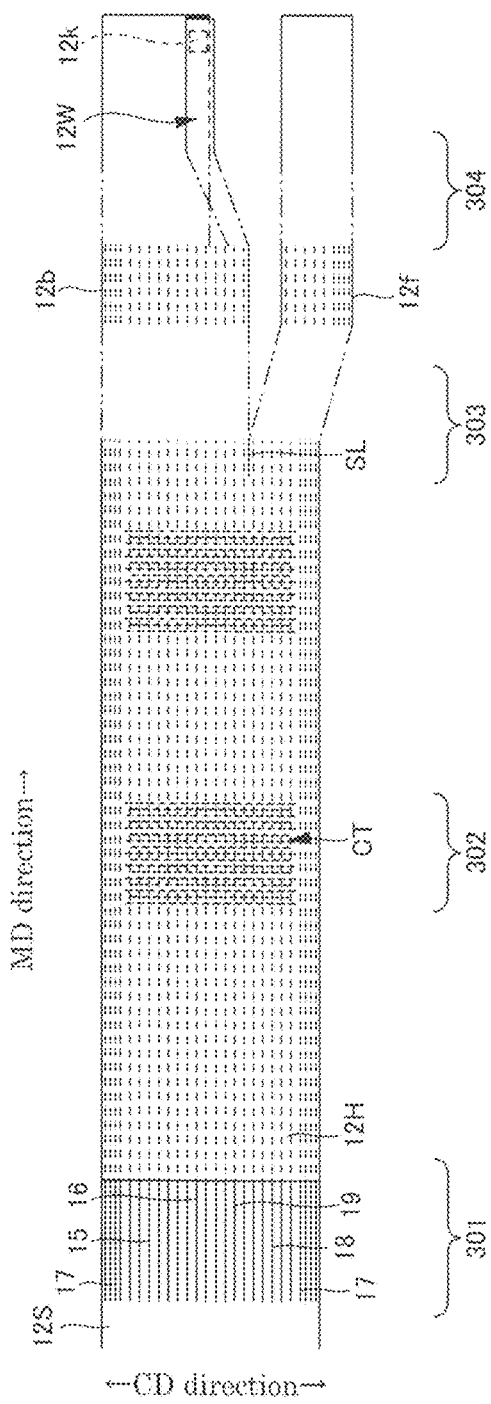
FIG. 14 is a plane diagram describing a production flow.
Figure 15:
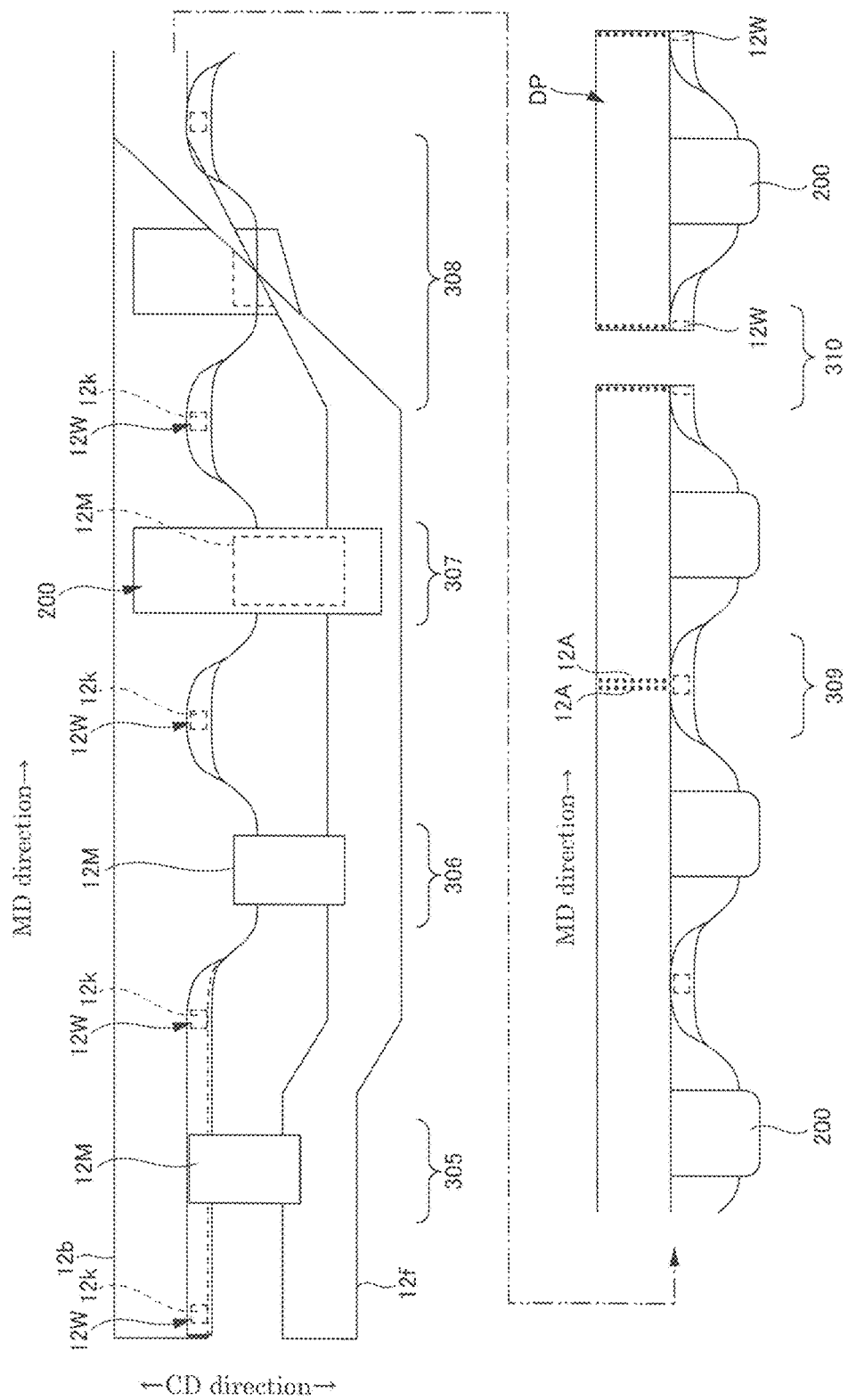
FIG. 15 is a plane diagram describing the production flow.
Figure 16:
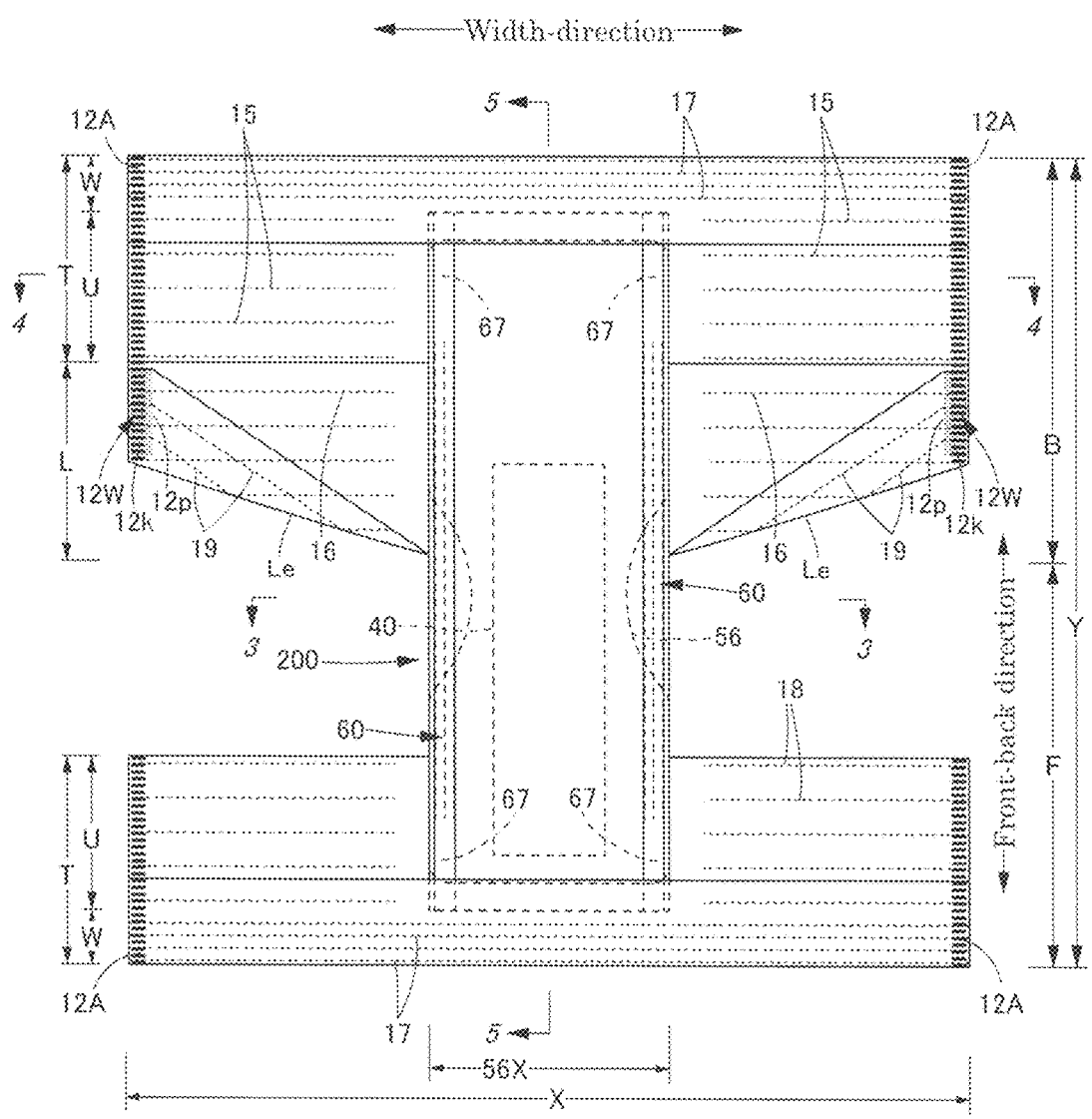
FIG. 16 a plane view of an inner surface of an underpants-type disposable diaper in an open state.
Figure 17:
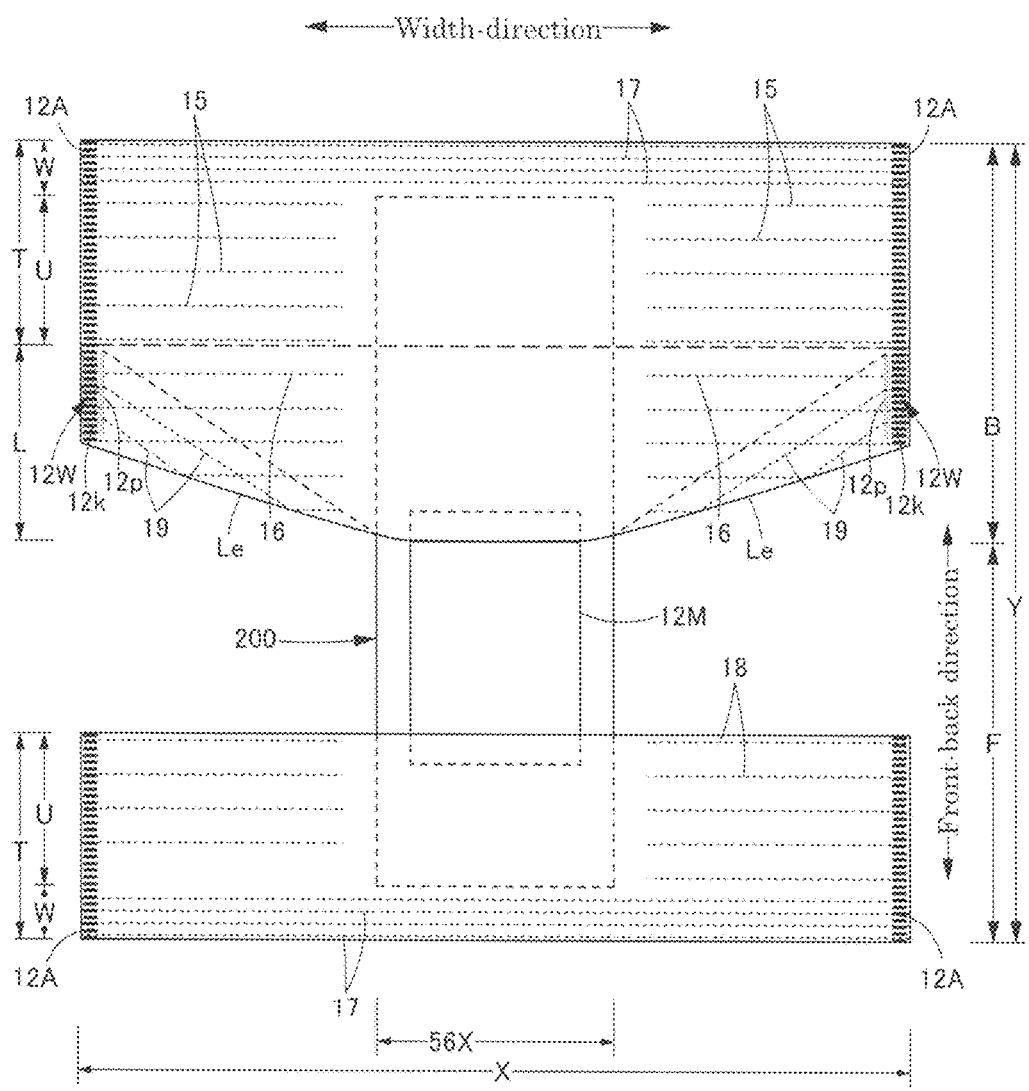
FIG. 17 is a plane view of an outer surface of an underpants-type disposable diaper in the open state.
Figure 18:
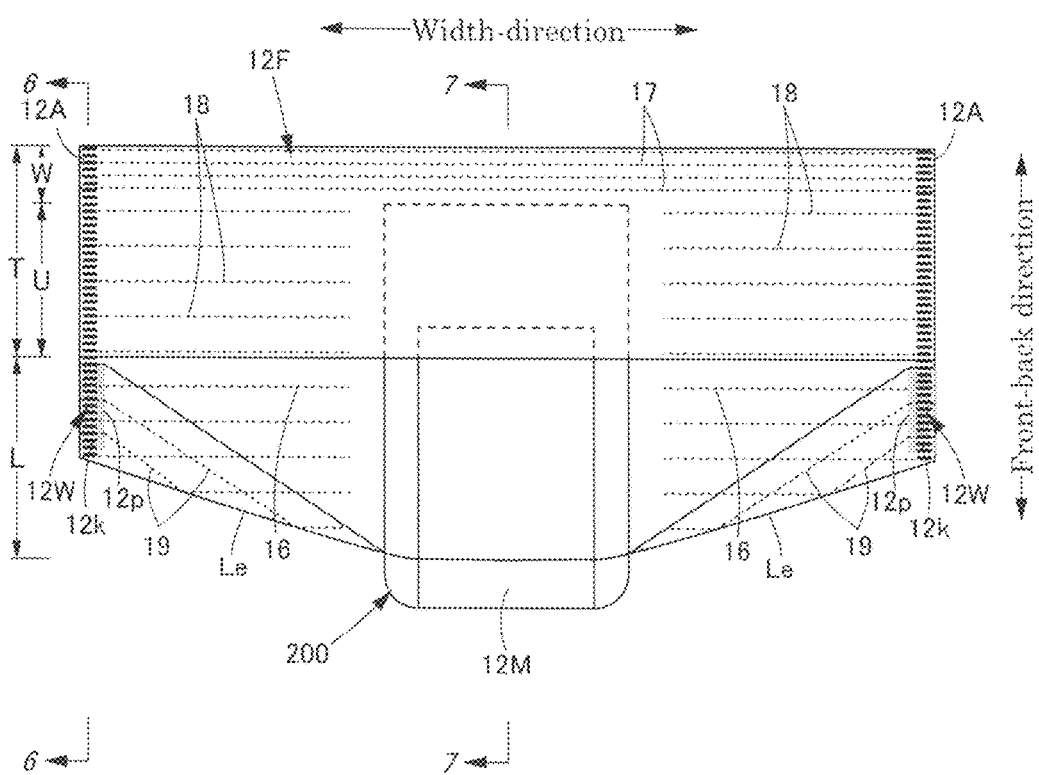
FIG. 18 is a front view of the underpants-type disposable diaper in the open state.
Figure 19:
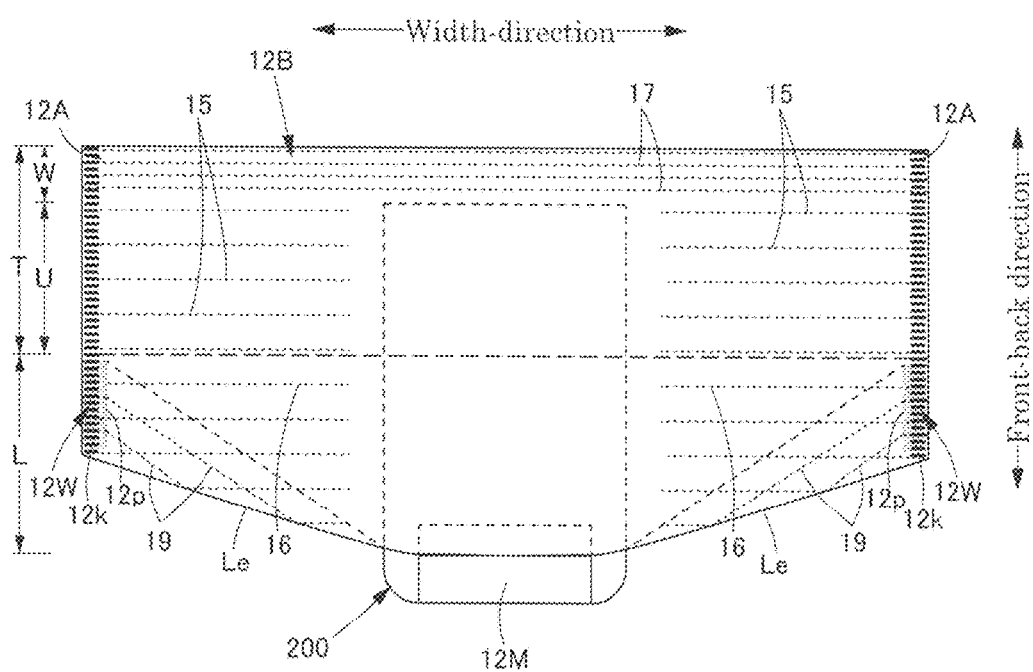
FIG. 19 is a back view of the underpants-type disposable diaper in the open state.

FIGS. 14 and 15 illustrate an example of a method for producing an underpants-type disposable diaper of the first form. This production line is formed for a lateral flow with the diaper width direction in parallel to the MD direction (machine direction or line flow direction). In this line, a ventral side elastic belt 12f that is to be a ventral side outer body 12F and a dorsal side elastic belt 12b that is to be a dorsal side outer body 12B are formed, and an inner body 200 produced in another line is attached to the ventral side elastic belt 12f and the dorsal side elastic belt 12b. For the sake of ease of understanding, the continuous members in the production process are given the same reference signs as those of the members after the production.

More specifically, the production line has a resilient member attachment step 301, a resilient member cutting step 302, a center slit step 303, a folding step 304, an inner body attachment step 305, a width increasing step 306, an inner body attachment step 307, a folding up step 308, and a side part joining step 309, and a cutoff step 310. Among these steps, the folding step 304 is more characteristic than the conventional production method.

Specifically, in the resilient member attachment step 301, while a belt-like sheet material 12H of predetermined width is conveyed in the continuous direction thereof, the elongated resilient members 15 to 19 such as rubber threads are fixed in an extended state in the MD direction, with spacing in the almost entire CD direction of the sheet material 12H. Furthermore, a belt-like material 12S of predetermined width is supplied along the continuous direction thereof to top surfaces of the elongated elastic members and stuck thereto to form an elastic belt. In the illustrated example a form is assumed in which two sheet materials 12S and 12H are stuck to sandwich the resilient and elastic members 15 to 19. However, the resilient and elastic members may also be sandwiched by folding one sheet material double or in C form.

Then, the resilient member cutting step 302 is carried out on the formed elastic belt, as needed. With predetermined spacing in the MD direction, the resilient and elastic members 15, 16, 18, and 19 positioned at a portion CT that will later overlap the inner body 200 are cut by a cutting device such as heat embossing device so that the stretching force of the resilient and elastic members 15, 16, 18, and 19 do not act on the portion CT.

Then, in the outer bodies 12F and 12B cutting and splitting step 303, an intermediate predetermined region SL of the elastic member in the CD direction is cut along the MD direction to split the member into the ventral side elastic belt 12f and the dorsal side elastic belt 12b and expand spacing between the ventral side elastic belt 12f and the dorsal side elastic belt 12b to a predetermined distance. After the slitting, although a side edge (that is to be an edge Le of a leg opening) at the center side in the CD direction of at least one of the ventral side elastic belt 12f and the dorsal side elastic belt 12b may be cut off in a curved manner, as needed, such cutting is not carried out if trim loss is completely eliminated. Nevertheless, as described later, the edge Le of the leg opening may be formed so as to be along an oblique direction. In addition, in the illustrated example, the ventral side elastic belt 12f and the dorsal side elastic belt 12b are split separately in the cutting and splitting step 303 after being formed as an integrated elastic belt. However, by using different sheet materials to form the ventral side elastic belt 12f and the dorsal side elastic belt 12b, it is possible to omit the cutting and splitting step 304, and in doing so, the resilient and elastic members may be sandwiched by sticking two sheet materials as well as by folding one sheet material double or in C form.

Then, at the folding step 304, while the ventral side elastic belt 12f and the dorsal side elastic belt 12b are conveyed in parallel with a space therebetween in a CD direction, the edge side portion of the dorsal side elastic belt 12b on the ventral side elastic belt 12f side is folded once or plural times in a zigzag manner in the CD direction and fixed to form the folded part 12W. The fixed portion 12k of the folded part 12W can be formed by an appropriate joining means such as a hot-melt adhesive or heat sealing. Although not illustrated, in the case of providing the folded part 12W of the present invention on the ventral side as well, the edge side portion of the ventral side elastic belt 12f on the dorsal side elastic belt 12b side is also folded once or plural times in a zigzag manner in the CD direction to form the folded part. Although there is no particular limitation on the number of folds in the folded part 12W as described above, the even number is advantageous because the portion of the folded part 12W closer to the forward edge than to the fold closest to the forward edge is faced to the opposite elastic belt (ventral side elastic belt). Accordingly, when the folded part 12W is unfolded by the connecting member 12M at the connecting step described later, no force acts in the detachment direction, and therefore the connecting is stable and turn-up or detachment is unlikely to occur.

Then, at the connecting step 305, the portion of the folded part 12W closer to the forward edge than to the fold closest to the forward edge is connected to the opposite elastic belt by the connecting member with a predetermined space in a MD direction. That is, in the case of providing the folded part 12W in the dorsal side elastic belt 12b as in the illustrated form, the portion of the folded part 12W in the dorsal side elastic belt closer to the forward edge than to the fold closest to the forward edge is connected to the ventral side elastic belt 12f by the connecting member 12M. In the case of providing the folded part 12W in the ventral side elastic belt 12f, not in the dorsal side elastic belt 12b, the portion of the folded part 12W in the ventral side elastic belt 12f closer to the forward edge than to the fold closest to the forward edge is connected to the dorsal side elastic belt 12b by the connecting member. In the case of providing the folded part 12W in both the dorsal-side elastic belt 12b and the ventral side elastic belt 12f, the portion of the folded part 12W in the dorsal side elastic belt 12b closer to the forward edge than to the fold closest to the forward edge and the portion of the folded part 12W in the ventral side elastic belt 12f closer to the forward edge than to the fold closest to the forward edge are connected by the connecting member. The connecting can be performed by an appropriate joining means such as a hot-melt adhesive or heat sealing. The connecting member 12M may be a member dedicated for connecting, and in that case, there is no particular limitation on the shape and dimension of the connecting member 12M. However, the connecting means 12M in the illustrated form has a certain degree of width and is assumed to become the crotch cover sheet 12M described above in the diaper product.

Subsequently to the connecting step 305, at the width increasing step 306, a relative space between the ventral side elastic belt 12f and the dorsal side elastic belt 12b in the CD direction is increased, and the portion of the folded part 12W connected by the connecting member 12M is pulled to unfold the folded part 12W halfway or completely. Accordingly, the oblique edge of the dorsal side elastic belt 12b becomes the edges Le of the leg openings.

After that, at the inner body attachment step 307, the inner body 200 produced in advance in another production line is supplied at predetermined intervals in the MD direction, a front part of the inner body 200 is joined to the ventral side elastic belt 12f and a back part of the inner body 200 is joined to the dorsal side elastic belt 12b, and the unfolded portion of the folded part is fixed to the inner body 200 to form an inner assembly body. The inner body is desirably fixed to the connecting member 12M as well. These joining and fixation can be performed by an appropriate means such as a hot-melt adhesive or heat sealing.

Then, at the folding up step 308, the inner assembly body is folded at center in the CD direction such that an attachment surface of the ventral side elastic belt 12f relative to the inner body 200 and an attachment surface of the dorsal side elastic belt 12b relative to the inner body 200 overlap. After that, at the side part joining step 309, the ventral side elastic belt 12f and the dorsal side elastic belt 12b are joined by parts to be both sides of each individual diaper to form the side seal portions 12A. At the cutoff step 310, the ventral side elastic belt 12f and the dorsal side elastic belt 12b are cut off at boundaries of each individual diaper, thereby obtaining each individual diaper DP. The side part joining step 309 and the cutoff step 310 can be performed simultaneously.

In the thus produced disposable diaper, the edges Le of the leg openings in the dorsal side outer body 12B positioned on the lateral sides of the inner body 200 are faced in an obliquely upward direction toward the side edge portions, and the oblique resilient and elastic members 19 are fixed in an extended state along the edges. Accordingly, the edges Le of the leg openings fit favorably around the buttocks of the wearer without slack. In addition, the formation of the leg openings does not need cutting, which eliminates completely trim loss in the production of the outer bodies 12F and 12B. Further, without the use of a so-called swing device, the oblique resilient and elastic members 19 can be provided in an oblique direction in the product.

To produce the underpants-type disposable diaper having the outer body 12 continuous from the ventral side to the dorsal side via the crotch as illustrated in FIG. 13, out of steps 301 to 310 in the foregoing production method, at least the center slit step 303 and the connecting step 305 are not provided but a punching step for forming leg openings in one large elastic belt is provided instead. In this case, cut pieces are generated but the connecting member 12M is not needed. The punching step may be provided at any stage between the steps 301 to 310, but is preferably provided between the resilient member cutting step 302 and the folding step 304.

Figure 25:
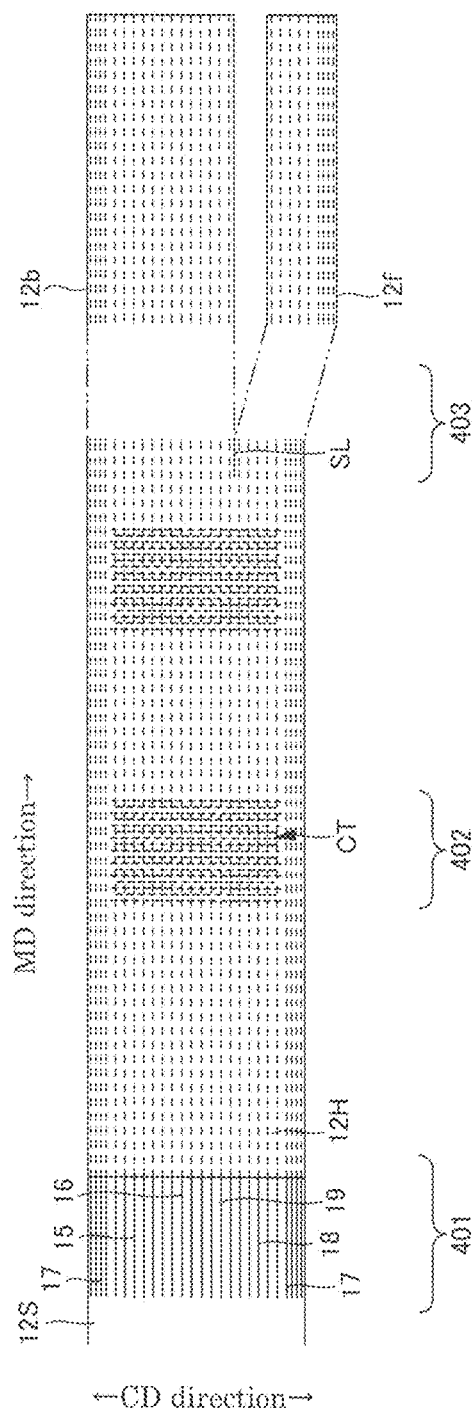
FIG. 25 is a plane diagram describing a production flow.
Figure 26:
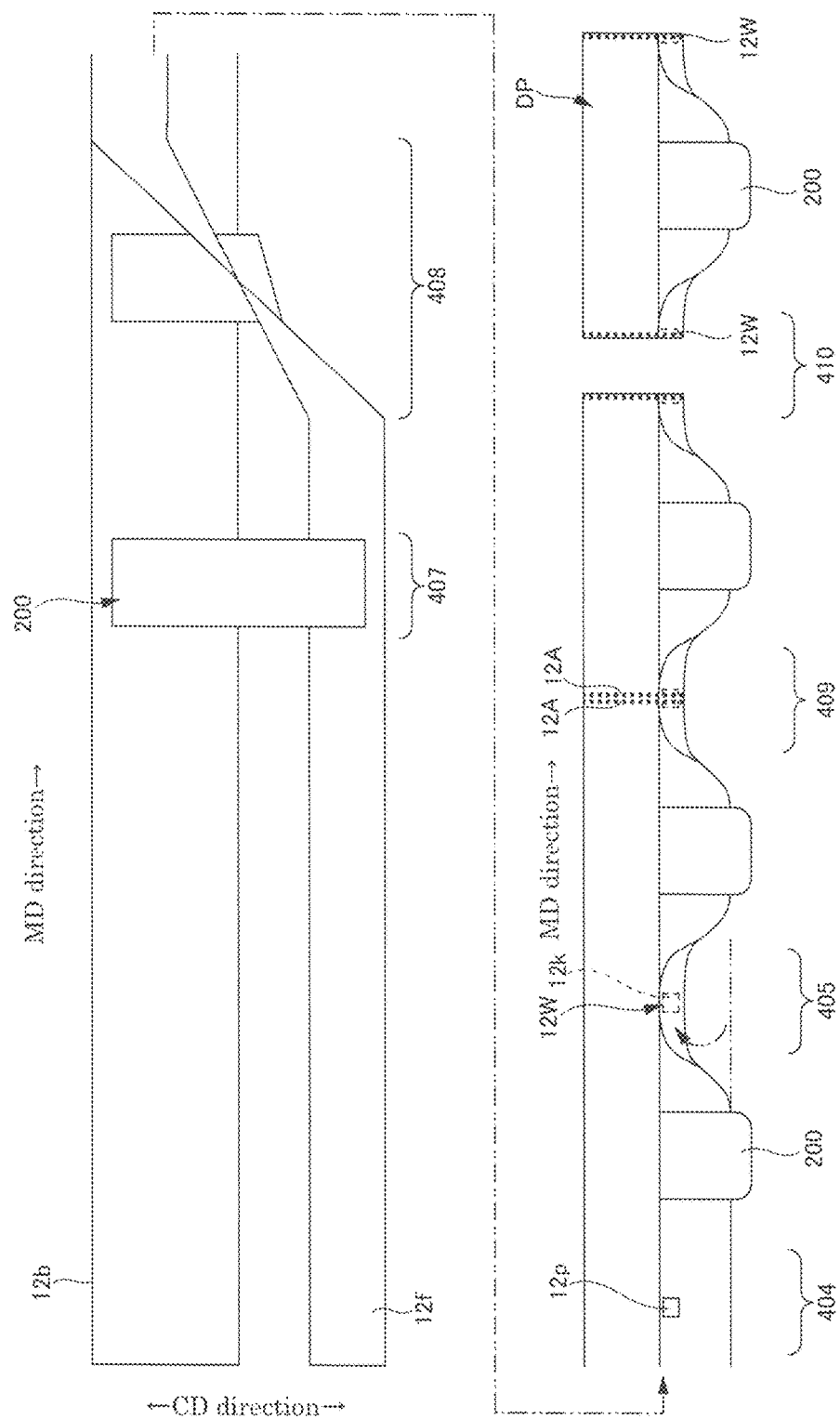
FIG. 26 is a plane diagram describing the production flow.

FIGS. 25 and 26 illustrate an example of a production method by which the side seal portions 12A and the folded part 12W are welded integrally. The production line is formed for a lateral flow with the diaper width direction in parallel to the MD direction (machine direction or line flow direction). In the production line, the ventral side elastic belt 12f to be the ventral side outer body 12F and the dorsal side elastic belt 12b to be the dorsal side outer body 12B are formed, and the inner body 200 produced in another line is attached to the ventral side elastic belt 12f and the dorsal-side elastic belt 12b. For ease of understanding, in the following description, the members continuous in the production process are given the same reference signs of the members after the production.

More specifically, the production line includes a resilient member attachment step 401, a resilient member cutting step 402, an outer body cutting and splitting step 403, an inner body attachment step 407, a folding up step 408, an adhesive application step 404, a folding step 405, and a side part joining step 409, a cutoff step 410. Among these steps, the folding step 405 is characteristic in particular as compared to the conventional production method.

Specifically, at the resilient member attachment step 401, while the belt-like sheet material 12S of a predetermined width is conveyed along the continuous direction thereof, the resilient and elastic members 15 to 19 such as rubber threads are fixed in an extended state in the MD direction to almost the entire sheet material 12S at a space therebetween in the CD direction, and the belt-like sheet material 12H of a predetermined width is supplied and stuck to the upper surface of the sheet material 12S along the continuous direction thereof, thereby forming the elastic belt. In the illustrated example, the two sheet materials 12S and 12H are stuck to sandwich the resilient and elastic members 15 to 19. Alternatively, one sheet material may be folded double or in C form to sandwich the resilient and elastic members. In addition, at least one end of one sheet material in the CD direction may be folded toward the back side (opposite to the opposed surface) of the other sheet material.

Then, the resilient member cutting step 402 is performed as needed on the formed elastic belt to cut by a cutting device such as a heat embossing device the resilient and elastic members 15, 16, 18, and 19 positioned at the portion CT to overlap the inner body 200 later at a predetermined space therebetween in the MD direction so that the stretching force of the resilient and elastic members 15, 16, 18, and 19 does not act on the portion CT.

Next, at the outer body cutting step 403, a predetermined central site SL of the elastic belt in the CD direction is cut by a slitter along the MD direction to split the elastic belt into the ventral side elastic belt 12f and the dorsal side elastic belt 12b, and the space between the ventral side elastic belt 12f and the dorsal side elastic belt 12b is increased to a predetermined distance. After the formation of the slit, a CD direction central side edge (to be the edges Le of the leg openings) of at least one of the ventral side elastic belt 12f and the dorsal side elastic belt 12b may be cut in a curved shape as necessary. However, the cutting is not to be performed to eliminate completely trim loss. Nevertheless, the edges Le of the leg openings can be shaped in an oblique direction as described later. In addition, in the illustrated example, the integrally-formed elastic belt is split into the ventral side elastic belt 12f and the dorsal side elastic belt 12b at the cutting and splitting step 403. Alternatively, the ventral side elastic belt 12f and the dorsal side elastic belt 12b may be formed from separate sheet materials to omit the cutting and splitting step 404. In this case as well, the two sheet materials may be stuck to sandwich the resilient and elastic members, one sheet material may be folded double or in C form to sandwich the resilient and elastic members, or at least one end of one of the sheet materials in the CD direction may be folded toward the back side (opposite of the opposed surface) of the other sheet material.

Then, at the inner body attachment step 407, while the ventral side elastic belt 12f and the dorsal side elastic belt 12b are conveyed in parallel with a space therebetween in the CD direction, the inner body 200 produced in a simultaneous parallel manner in another line by a publicly known method is supplied at predetermined intervals in the MD direction, and the front part of the inner body 200 is joined to the ventral side elastic belt 12f and the back part of the inner body 200 is joined to the dorsal side elastic belt 12b, thereby forming the inner assembly body. These joining and fixing operations can be performed by an appropriate means such as a hot-melt adhesive or heat sealing.

Then, at the folding step 408, the inner assembly body is folded at center in the CD direction such that the attachment surface of the ventral side elastic belt 12f relative to the inner body 200 and the attachment surface of the dorsal side elastic belt 12b relative to the inner body 200 overlap.

Then, at the adhesive application step 404, the adhesive 12p such as a hot-melt adhesive is applied to the leg opening side portion of the dorsal side elastic belt 12b at a folded part formative position with a predetermined space in the MD direction. After that, at the folding step 405, the leg opening side portion of the dorsal side elastic belt 12b is folded in the CD direction and fixed with the previously applied adhesive 12p, thereby forming the folded part 12W. Accordingly, the oblique edge of the dorsal side elastic belt 12b constitutes the edges Le of the leg openings.

After that, at the side part joining step 409, the ventral side elastic belt 12f and the dorsal side elastic belt 12b are joined at the both sides of each individual diaper to form the side seal portions 12A. At the cutoff step 410, the ventral side elastic belt 12f and the dorsal side elastic belt 12b are cut at boundaries of each individual diaper to obtain each individual diaper DP. According to the present invention, the side part joining step 409 and the cutoff step 410 may be performed in sequence or simultaneously. At the side part joining step 409, the side seal portions 12A and the folded part 12W may be welded integrally as in the illustrated form, or when the folded part 12W is positioned under the side seal portions 12A, the folded part 12W may not be welded. The structure and advantages of the thus produced disposable diaper are as follows.

In this example, the adhesive application step 404 and the folding step 405 are performed between the folding up step 408 and the side part joining step 409. Alternatively, the adhesive application step 404 and the folding step 405 may be performed anywhere between the inner body attachment step 407 and the cutoff step 410.

Figure 24:
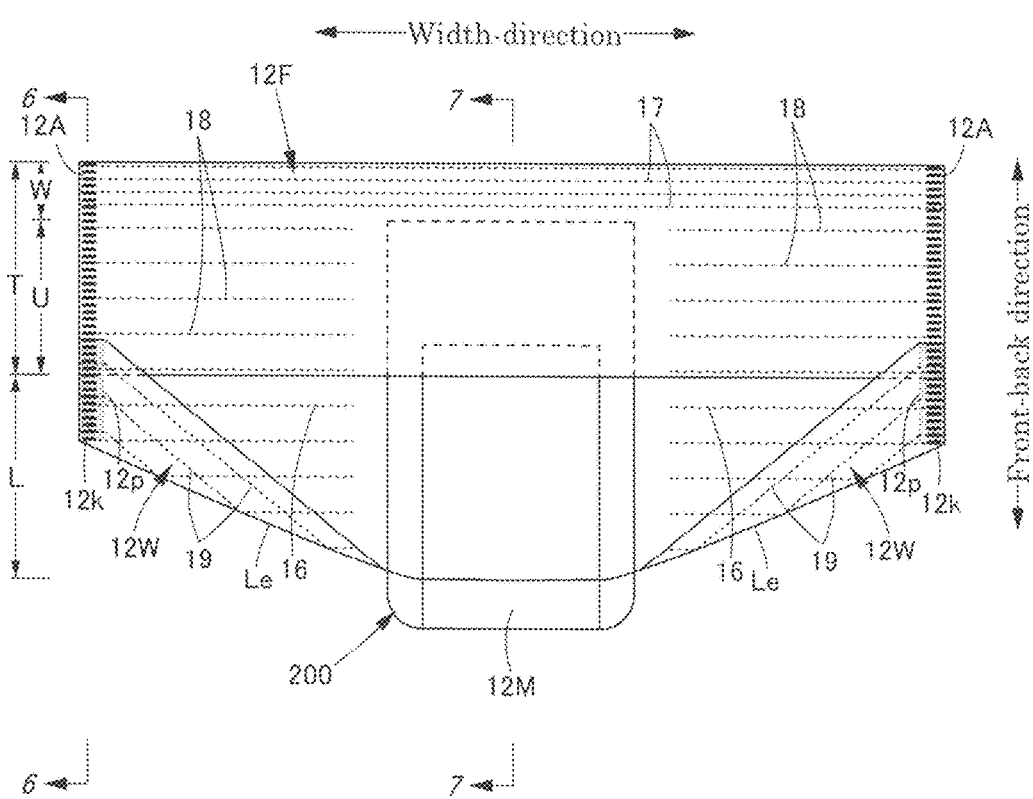
FIG. 24 is a front view of the underpants-type disposable diaper in the open state.
Figure 27:
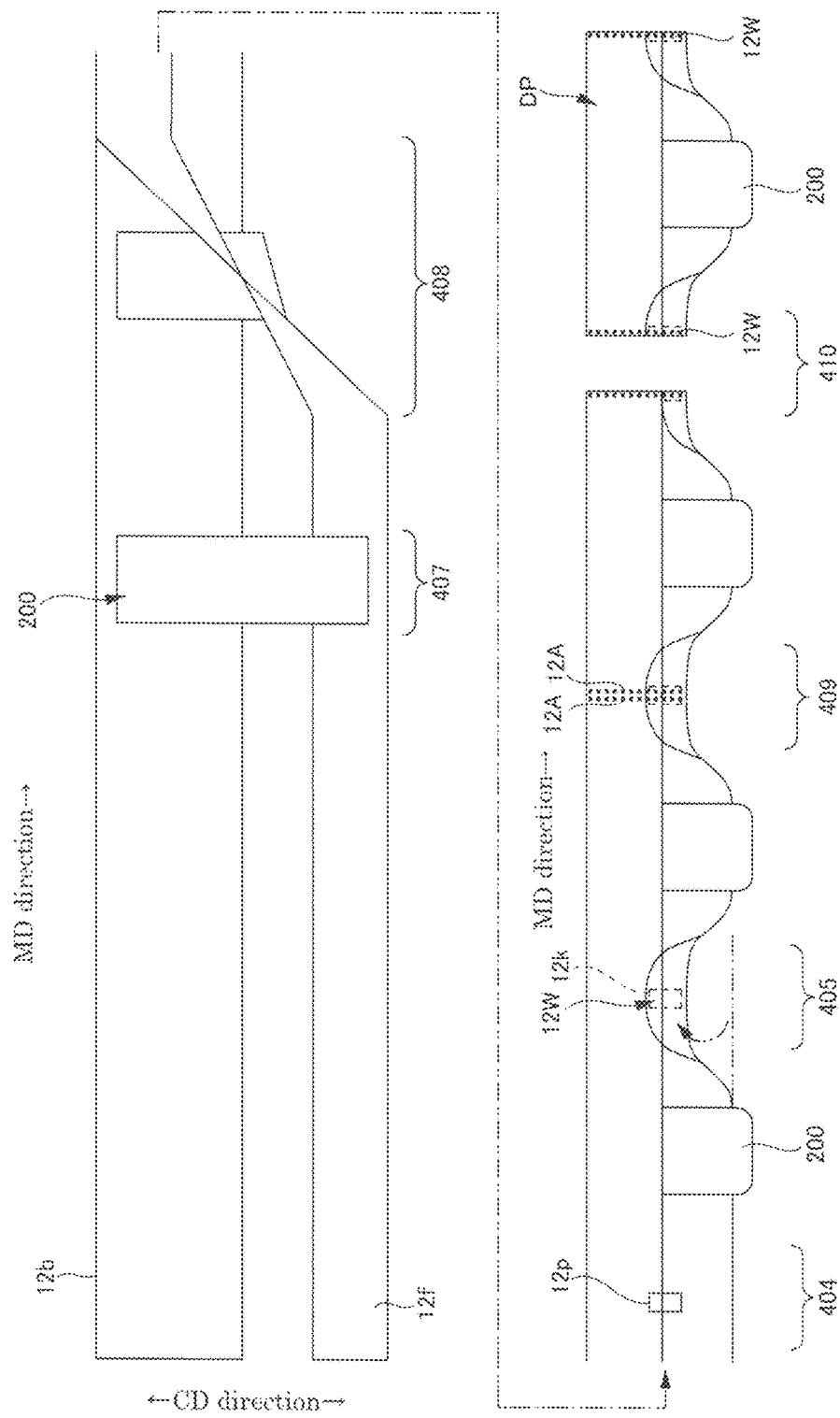
FIG. 27 is a plane diagram describing the production flow.

FIG. 27 illustrates a production flow of forming the folded part 12W in the form illustrated in FIG. 24. At the folding step 405, the leg opening side portion of the dorsal side elastic belt 12b is folded in the CD direction over the ventral side elastic body 12f, and is fixed with the previously applied adhesive 12p to form the folded part 12W. This form is suitable for the case in which the angle of the edges Le of the leg openings is to be higher. In this form, the adhesive application step 404 and the folding step 405 are performed after the folding up step 408. In the other respects, this form is the same as the form illustrated in FIGS. 25 and 26.

Figure 28:
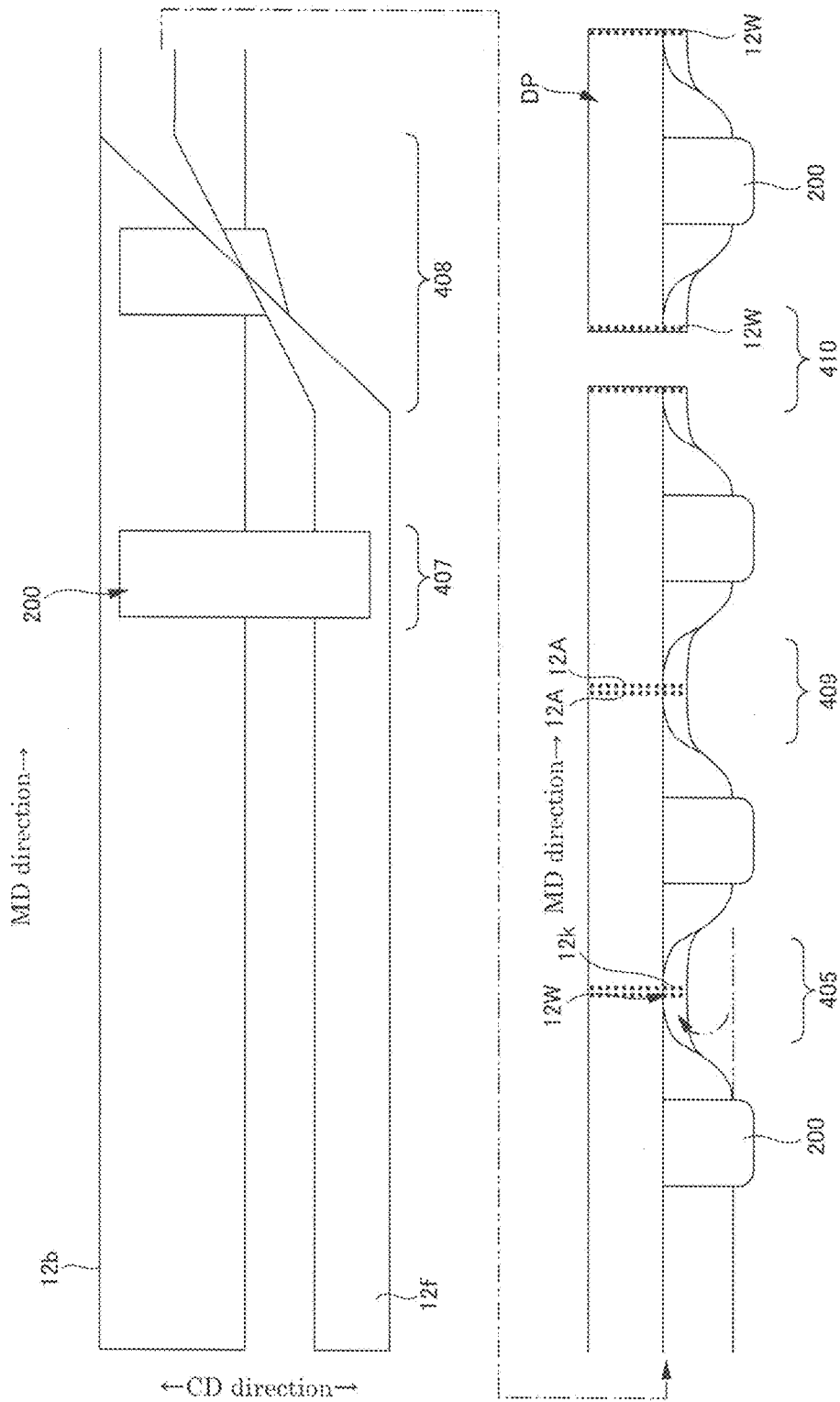
FIG. 28 is a plane diagram describing the production flow.

FIG. 28 illustrates a production flow of forming the folded part 12W in the form illustrated in FIG. 23. The adhesive application step 404 is omitted. At the folding step 405, while the folded state is held, the joining of the ventral side elastic belt 12f and the dorsal side elastic belt 12b and the fixation of the folded part 12W are performed simultaneously by welding at the side part joining step 409. This provides advantages that the production method can be simplified, the material cost can be reduced by the reduction in the use of the adhesive, and the hardening of the outer bodies 12F and 12B can be suppressed by the reduction in the use of the adhesive. In the other respects, this form is the same as the form illustrated in FIGS. 25 and 26.

Although not illustrated, when the folded part 12W is to be provided in the ventral side, at the folding step 405, the leg opening side portion of the ventral side elastic belt 12*f* is folded in the CD direction and fixed to form the folded part.

In addition, although not illustrated, in the case of producing an underpants-type disposable diaper having the outer body 12 continuous from the ventral side to the dorsal side via the crotch, at least the center slit step 403 is not provided in the foregoing production method including the steps 401 to 410. Instead of this, a punching step is provided to form leg openings in one large elastic belt. The punching step may be provided at any stage, but is preferably provided between the resilient member attachment step 401 and the inner body attachment step 407.

<Descriptions of the Terms Used Herein>

Unless otherwise specified herein, the terms used herein have the meanings described below.

"front-back (vertical) direction" refers to the direction linking the ventral side (front side) and the dorsal side (back side), and the "width direction" refers to the direction (right-left direction) orthogonal to the front-back direction. The "up-down direction" refers to the direction that becomes orthogonal to the waist direction when the diaper is worn, that is, when the diaper is folded into two at the crotch portion such that the front panel and the back panel are overlapped at the both sides, in other words, the direction linking a waist opening and a crotch portion.

The "extension ratio" refers to a value with respect to 100% representing the natural length.

The "basis weight" is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$.

The water absorption capacity is measured by carrying out JIS K7223-1996 "Testing method for water absorption capacity of super absorbent polymers."

The water absorption rate is defined as "time that elapses before the end point" by carrying out JIS K7224-1996 "Testing method for water absorption rate of super absorbent polymers" using 2 g of high absorbent polymer and 50 g of saline.

If there is no description on environmental conditions in testing or measurements, the testing or the measurements shall be conducted in a test room or within a device under a normal state (a place of test shall be at temperatures of 20±5° C. and relative humidity of 60% or less).

INDUSTRIAL APPLICABILITY

The present invention is usable to an underpants-type disposable diaper and a production method therefor.

REFERENCE SIGNS LIST

L Intermediate portion
Le Edge of leg opening
T Waist portion
U Lower waist portion
W Waist edge portion
Liquid impervious sheet
12A Side seal portion
12B Dorsal side outer body
12F, 12B Outer body
12F Ventral side outer body
12H Inner sheet material
12M Crotch portion cover sheet
12S, 12H Sheet material
12S Outer sheet material
12W Folded part
12*b* Dorsal side elastic belt
12*c* CD direction intermediate portion
12*d* Separation portion
12*e* Edge sheet material
12*f* Ventral side elastic belt
12*w* Overlapped portion
15 to 19 Elongated resilient and elastic member
16 Intermediate portion resilient and elastic member
27 Waist edge portion resilient and elastic member
19 Oblique resilient and elastic member
30 Top sheet
50 Absorbent element
56 Absorber
58 Wrapping sheet
60 Three-dimensional gather
62 Gather sheet
200 Inner body
301 Resilient member attachment step
302 Resilient member cutting step
303 Center slit step
304 Leg opening cutting and splitting step
305 Inner body attachment step
306 Folding up step
307 Side part joining step
308 Cutoff step
401 Resilient member attachment step
402 Resilient member cutting step
403 Center slit step
404 Adhesion application step
405 Folding step
407 Inner body attachment step
408 Folding up step
409 Side part joining step
410 Cutoff step

The invention claimed is:

1. An underpants-type disposable diaper comprising:
an outer body that has a ventral side outer part and a dorsal side outer part and a waist opening formed by joining side edge portions of the ventral side outer part and side edge portions of the dorsal side outer part at both width direction sides; and
an inner body that has a front part joined to a width-direction central area of the ventral side outer body and a back part joined to a width-direction central area of the dorsal side outer body and configured to pass through the crotch of a wearer, edges of leg openings being at least partially formed by edges of parts of the outer body positioned on width-direction both sides of the inner body,
wherein in at least one of the ventral side outer part and the dorsal side outer part, parts at a lower edge of a side edge correspondence region corresponding to the side edge portions in a front-back direction, positioned on the both width direction sides of the inner body, constitute the edges of the leg openings, a lower part of the side edge correspondence region is set as a folded part that is folded once or plural times in a zigzag manner in the front-back direction and fixed at the side edge portions, the folded part is gradually unfolded downward with increasing proximity to the width-direction central side, and the folded part is fixed in a halfway or completely downward unfolded state to the inner body at the width direction central portion, and elongated oblique resilient and elastic members are fixed in an extended state in a direction from the folded part to the side edges of the inner body below the folded part.

2. The underpants-type disposable diaper according to claim 1, wherein the joining between the side edge portions of the ventral side outer part and the side edge portions of the dorsal side outer part and the fixation of the folded part are integrally performed by welding process.

3. The underpants-type disposable diaper according to claim 1, wherein the side edge portions of the ventral side outer part and the side edge portions of the dorsal side outer part are joined by welding but are not joined by the welding at least in a region having the folded part.

4. The underpants-type disposable diaper according to claim 1, wherein the outer body is formed by joining the ventral side outer body constituting the ventral side outer part and the dorsal side outer body constituting the dorsal side outer part at both sides, and the ventral side outer body and the dorsal side outer body are separated from each other without being continuous at the crotch side.

5. The underpants-type disposable diaper according to claim 4, wherein the shape of at least one of the outer parts is rectangular with the folded part in the unfolded state.

6. The underpants-type disposable diaper according to claim 4, wherein the folded part is formed by being folded toward the inside of at least one of the outer parts.

7. The underpants-type disposable diaper according to claim 4, wherein the folded part is formed by folding toward the outside of at least one of the outer parts.

8. The underpants-type disposable diaper according to claim 1, wherein the at least one of the outer parts is the dorsal side outer part.

9. The underpants-type disposable diaper according to claim 8, wherein the number of folds in the folded part is an even number.

10. The underpants-type disposable diaper according to claim 1, wherein the at least one of the outer parts is the ventral side outer part, and the number of folds in the folded part is an odd number.

11. The underpants-type disposable diaper according to claim 1, wherein the folded part is formed in one of the outer parts, and the folded part is extended over the outside of the other outer part.

12. A production method for an underpants-type disposable diaper, comprising:
an elastic belt formation step of forming a ventral side elastic belt and a dorsal side elastic belt in which elongated resilient and elastic members are fixed in an extended state to a belt-like continuous sheet material along a continuous direction thereof;
a folding step of, while conveying the ventral side elastic belt and the dorsal side elastic belt in parallel with a space therebetween in a CD direction, folding and fixing an edge side portion of at least one of the elastic belts on the side facing the other elastic belt once or plural times in a zigzag manner in the CD direction to form a folded part;
a connecting step of, after the folded part formation step, connecting a portion of the folded part closer to the forward edge than to the fold closest to the forward edge to the other elastic belt by a connecting member with a predetermined space in a MD direction;
a width increasing step of, after the connecting step, increasing relative space between the ventral side elastic belt and the dorsal side elastic belt in the CD direction, pulling the portion of the folded part connected by the connecting member to unfold the folded part halfway or completely;
an inner body attachment step of supplying a separately produced inner body at intervals in the MD direction and joining a front part of the inner body to the ventral side elastic belt and a back part of the inner body to the dorsal side elastic belt, and fixing the unfolded portion of the folded part in the unfolded state to the inner body to form an inner assembly body;
a folding step of folding double the inner assembly body in the CD direction; and
a side part joining and cutoff step of joining the ventral side elastic belt and the dorsal side elastic belt at both side parts of each individual diaper, and cutting off the ventral side elastic belt and the dorsal side elastic belt at boundaries of each individual diaper to obtain each individual diaper.

13. The production method for the underpants-type disposable diaper according to claim 12, wherein the number of folds is an even number at the folded part formation step.

14. A production method for an underpants-type disposable diaper, comprising:
an elastic belt formation step of forming a ventral side elastic belt and a dorsal side elastic belt in which elongated resilient and elastic members are fixed in an extended state to a belt-like continuous sheet material along a continuous direction thereof;
an inner body attachment step of, while conveying the ventral side elastic belt and the dorsal side elastic belt in parallel with a space therebetween in a CD direction, supplying a separately produced inner body at intervals in a MD direction, and joining a front part of the inner body to the ventral side elastic belt and a back part of the inner body to the dorsal side elastic belt to form an inner assembly body;
a folding step of folding double the inner assembly body in the CD direction; and
a side part joining and cutoff step of joining the ventral side elastic belt and the dorsal side elastic belt at both side parts of each individual diaper, and cutting off the ventral side elastic belt and the dorsal side elastic belt at boundaries of each individual diaper to obtain each individual diaper, wherein
the production method further includes, after the inner body attachment step and before cutting at the boundaries of each individual diaper, a folding step of folding and fixing a portion on the leg opening side of at least one of the elastic belts once or plural times in a zigzag manner in the CD direction to form a folded part.

15. The production method for the underpants-type disposable diaper according to claim 14, wherein, prior to the folding step, an adhesive is applied to a site for fixing the folded part of the at least one elastic belt to fix the folded part with the adhesive at the folding step.

16. The production method for the underpants-type disposable diaper according to claim 14, wherein, prior to the joining of the ventral side elastic belt and the dorsal side elastic belt at the side part joining and cutoff step, the folding at the folding step is performed, and while the folded state is held, the joining of the ventral side elastic belt and the dorsal side elastic belt and the fixation of the folded part are performed simultaneously by welding process.

* * * * *